US007081460B2

(12) United States Patent
Hoekstra et al.

(10) Patent No.: US 7,081,460 B2
(45) Date of Patent: Jul. 25, 2006

(54) QUINAZOLINE AND QUINAZOLINE-LIKE COMPOUNDS FOR THE TREATMENT OF INTEGRIN-MEDIATED DISORDERS

(75) Inventors: William J. Hoekstra, Chapel Hill, NC (US); Edward C. Lawson, Pipersville, PA (US); Michael J. Costanzo, Ivyland, PA (US)

(73) Assignee: Ortho-McNeil Pharmaceutical, Inc., Raritan, NY (US)

( * ) Notice: Subject to any disclaimer, the term of this patent is extended or adjusted under 35 U.S.C. 154(b) by 540 days.

(21) Appl. No.: 10/117,542

(22) Filed: Apr. 5, 2002

(65) Prior Publication Data

US 2003/0139398 A1 Jul. 24, 2003

Related U.S. Application Data

(60) Provisional application No. 60/282,648, filed on Apr. 9, 2001.

(51) Int. Cl.
*C07D 239/90* (2006.01)
*A61K 31/517* (2006.01)
*A61P 25/00* (2006.01)

(52) U.S. Cl. .............................. 514/266.1; 514/266.2; 544/287; 544/283

(58) Field of Classification Search ................ 544/283, 544/287; 514/259, 266.1, 266.2
See application file for complete search history.

(56) References Cited

U.S. PATENT DOCUMENTS

| 4,288,362 | A | 9/1981 | Rolf et al. |
| 5,352,667 | A | 10/1994 | Lider et al. |
| 5,576,334 | A | 11/1996 | Brown et al. |
| 5,602,155 | A | 2/1997 | Ruminski |
| 5,648,368 | A | 7/1997 | Egbertson et al. |
| 5,700,801 | A | 12/1997 | Pieper et al. |
| 5,703,050 | A | 12/1997 | Klingler et al. |
| 5,798,370 | A | 8/1998 | Ruminski |
| 5,817,677 | A | 10/1998 | Linz et al. |
| 5,922,717 | A | 7/1999 | Pieper et al. |
| 5,952,381 | A | 9/1999 | Chen et al. |
| 6,066,651 | A | 5/2000 | Hoekstra |
| 6,069,254 | A | 5/2000 | Contanzo et al. |
| 6,100,423 | A | 8/2000 | Collins et al. |
| 6,251,944 | B1 | 6/2001 | Chen et al. |
| 6,268,380 | B1 | 7/2001 | Tjoeng et al. |
| 6,617,330 | B1 * | 9/2003 | Walter ...................... 514/258.1 |

FOREIGN PATENT DOCUMENTS

| EP | 0373891 A2 | 6/1990 |
| JP | 4334357 A | 11/1992 |
| WO | WO 94/12181 A1 | 6/1994 |
| WO | WO 95/08536 A1 | 3/1995 |
| WO | WO 95/32710 A1 | 12/1995 |
| WO | WO 97/06791 A1 | 2/1997 |
| WO | WO 97/08145 A1 | 3/1997 |
| WO | WO 97/23451 A1 | 7/1997 |
| WO | WO 97/36859 A1 | 10/1997 |
| WO | WO 97/41102 A1 | 11/1997 |
| WO | WO 98/16512 A1 | 4/1998 |
| WO | WO 98/25892 A1 | 6/1998 |
| WO | WO 98/39325 A1 | 9/1998 |
| WO | WO 99/16758 A1 | 4/1999 |
| WO | WO 99/25685 A1 | 5/1999 |
| WO | WO 99/67230 A1 | 6/1999 |
| WO | WO 99/50249 A2 | 10/1999 |
| WO | WO 99/58501 A1 | 11/1999 |
| WO | WO 00/11022 A1 | 3/2000 |
| WO | WO 01/10867 A1 | 2/2001 |

OTHER PUBLICATIONS

International Search Report for PCT/US02/10546 dated Apr. 5, 2002.
Biorganic & Medicinal Chemistry Letters, vol. 6, No. 20, pp 2371-2376, 1996-"Solid-Phase Parallel Synthesis Applied to Lead Optimization: Discovery of Potent Analogues of the GPIIb/llla Antagonist RWJ-50042".
Cox, D., Drug News & Perspectives, 1995, 8, "Integrin antagonists are a new challenge to the pharmaceutical industry and their development will require a multidisciplinary approach, with scientists from different areas working together. Targets in Integrin Research", pp. 197-205.
Gilon et al., Tetrahedron, 1967, 23, "Synthesis of ω-Aminooxy Acids by Oxygen-Alkyl Fission of Lactones", pp. 4441-4447.
Greenhill et al., Chem. Soc., Perkin Trans. 2, 1985 (8), "Conformational and Tautomeric Studies of Acylguanidines. Part 1. Synthesis, Utraviolet Spectroscopy, Tautomeric Preference, and Site of Protonation in Some Model Compounds", pp. 1255-1264.
Hershkovitz et al., Clinical Exp. Immunol. 1994: vol. 95, pp 270-276-"Inhibition of CD4+T lymphocyte binding to fibronection and immune-cell accumulation in imflammatory sites by non-peptidic mimetics of Arg-Gly-Asp".

(Continued)

*Primary Examiner*—Venkataraman Balasubramanian
(74) *Attorney, Agent, or Firm*—Hal B. Woodrow

(57) ABSTRACT

The invention is directed to novel quinazoline and quinazoline-like derivatives of Formula (I):

Formula (I)

useful as integrin antagonists and methods for the treatment of integrin-mediated disorders.

45 Claims, No Drawings

OTHER PUBLICATIONS

Hoekstra, Current Medicinal Chemistry, 1998, 5, "Combinatorial Chemistry Techniques Applied to Nonpeptide Integrin Antagonists", pp. 195-204.

Hosoda et al., "Preparation of N-(heterocycyclcarbonyl) amino Acids and Analogs as Prolyl Endopeptidase Inhibitors", Chemical Abstracts, vol. 118, No. 25, (1993), XP-002159418.

Keenan et al., Bioorg. Med. Chem. Lett, 1998, 8, "Discovery Of An Imidazopyridine-Containing 1,4-Benzodiazepine Nonpeptide Vitronnectin Receptor ($\alpha v\beta 3$) Antagonist With Efficacy In a Restenosis Model", pp. 3171-3176.

Ludwig et al., J. Med. Chem., 1970, 13, "Synthesis and Hypoglycemic Activity of Substituted Alkyl- and Alkoxyguanidines", pp. 60-63.

Mehta et al, Biochem J., 1998, 330, "Transmembrance-truncated $\alpha v\beta 3$ integrin retains high affinity for ligand binding: evidence for an 'inside-out' suppresor?", pp. 861-869.

Miller et al., Drug Discovery Today, 2000, 5 (9), "Identification and in vivo efficacy of small-molecule antagonists of integrin $\alpha v\beta 3$ (the vitronectin receptor)", pp. 397-408.

Mousa et al., Emerging Theraupeutic Targets, 2000, 4(2), " Integrins as novel drug-discovery targets: potential therapeutic and diagnostic implications", pp. 143-153.

Mousa et al., Exp. Opin. Ther. Patents, 1999, 9 (9), "Anti-integrins as a potential therapeutic target in angiogenesis", pp. 1237-1248.

Rico et al., J. Org. Chem., 1993, 58, "A Highly Stereoselective Michael Addition to an $\alpha,\beta$-Unsaturated Ester as the Crucial Step in the Synthesis of a Novel $\beta$-Amino Acid-Containing Fibrinogen Receptor Antagonist", pp. 7948-7951.

Samanen et al., Current Pharmaceutical Design, 1997, 3, "Vascular Indications for Integrin $\alpha v$ Antagonists", pp. 545-584.

Senanayake et al., Tetrahedron Lett., 1999, 40, "Properly tuned first fluoride-catalyzed TGME-mediated amination process for chloroimidazoles: inexpensive technology for antihistaminic norastemizole" pp. 6875-6879.

Su, Ting, "Sulfonamide Carboxylic Acid Function as Potent Platelet Aggregation Inhibitors", J. Med., Chem. (1997), pp. 4308-4318.

Varon et al., Thromb Haemostasis, 1993, 70(6), "Inhibition of Integrin-Mediated Platelet Aggregation Fibrinogen-Binding, and Interactions with Extracellular Matrix by Nonpeptidic Mimetics of Arg-Gly-Asp", pp. 1030-1036.

Archelos, J.J., et al., "The role of integrins in immune-mediated diseases of the nervous system", TNS, vol. 22, No. 1, 1999, pp. 30-38.

Cotman, C.W.. et al., "Cell Adhesion Molecules in Neural Plasticity and Pathology: Similar Mechanisms, Distinct Organizations?", Progress in Neurobiology, vol. 55, 1998, pp. 659-669.

Milner, R., "Understanding the molecular basis of cell migration; implications for clinical therapy in multiple sclerosis", Clinical Science, (1997) 92, pp. 113-122.

Fossati, G., et al., "In vitro effects of GM-CSF on mature peripheral blood neutrophils", International Journal of Molecular Medicine 1, 1998, pp. 943-951.

Hynes, R.O., "Integrins: Versatility, Modulation, and Signaling in Cell Adhesion", Cell, vol. 69, Apr. 3, 1992, pp. 11-25.

Lee, J., et al., Crystal Structure of the A Domain form the $\alpha$ Subunit of Integrin CR3 (CD11b/CD18); Cell, vol. 80, Feb. 24, 1995, pp. 631-638.

McCoy, L.E., "Basic Concepts of Hemostasis and thrombosis: Clinical and Laboratory Evaluation of Thrombohemorrhagic Phenomena", Murano, G., Bick, R.L. Eds.; CRC: Boca Raton, Florida, 1980, pp. 5-15.

Hughes, P.E., et al., "Integrin affinity modulation", Trends in Cell Biology, 1998, vol. 8, pp. 359-364.

Clover, J., et al., "Integrin subunit expression by human osteoblasts and osteoclasts in situ and in culture" Journal of Cell Science, 103, pp. 267-271.

Duggan, M.E., et al., "Nonpeptide of $\alpha_v\beta_3$ Antagonists 1 . Transformation of a Potent, Integrin-Selective $\alpha_{IIb}\beta_3$ Antagonist into a Potent $\alpha_v\beta_3$ Antagonist", J. Med. Chem, 2000, 43, pp. 3736-3745.

Attur, Mukundan G., "Functional Genomic Analysis in Arthritis-Affected Cartilage: Yin-Yang Regulation of Inflammatory Mediators by $\alpha_5\beta_1$ and $\alpha_v\beta_3$ Integrins", The Journal of Immunogoly, Copyright 2000 by The american Association of Immunologists, pp. 2684-2691.

Buckley, C.D., "Identification of $\alpha_v\beta_3$ as a heterotypic ligand for CD31/PECAM-1", Journal of Cell Science, 109, 1996, pp. 437-445.

Scaffidi, Amelia K., "Regulation of human lung fibroblast phenotype and function by vitronectin and vitronectin integrins", Journal of Cell Science, 114, 2001, pp. 3507-3516.

Fields, Gregg B., "Integrins: cell adhesion molecules in cancer", Exp. Opin. Ther. Patents (1998), 8(6), pp. 633-644.

Byzova, Tatiana V., et al., "Role of Integrin $\alpha_v\beta_3$ in Vascular Biology", Thromb. Haemost, (1998), 80, pp. 726-734.

Larksarp, Chitchamai et al., "Palladium-Catalyzed Cyclocarbonylation of o-Iodoanilines with Heterocumulenes: Regioselective Preparation of 4(3H)-Quinazoliinone Derivatives", J. Org. Chem. 200, 65, pp. 2773-2777.

* cited by examiner

QUINAZOLINE AND QUINAZOLINE-LIKE COMPOUNDS FOR THE TREATMENT OF INTEGRIN-MEDIATED DISORDERS

This application claims benefit of U.S. Provisional Patent Application Ser. No. 60/282,648, having the same title, filed on 9 Apr. 2001 (which is hereby incorporated by reference herein).

FIELD OF THE INVENTION

This invention is directed to certain novel compounds, their synthesis and their use for the treatment of integrin-mediated disorders. More particularly, this invention is directed to quinazoline and quinazoline-like compounds useful as integrin antagonists and methods for treating integrin-mediated disorders.

BACKGROUND OF THE INVENTION

Integrins are α or β heterodimeric cell surface receptors which bind to extracellular matrix adhesive proteins such as fibrinogen, fibronectin, vitronectin, and osteopontin. These transmembrane glycoproteins (GP's), known for their large extracellular domains, are classified by the β subunit. The β3 class of the integrin family has received the most attention in recent drug discovery efforts (W. J. Hoekstra, *Current Medicinal Chemistry*, 1998, 5, 195). Some of the disease states that have a strong β3 integrin component in their etiologies are thrombosis (integrin α2bβ3, also called GPIIb/IIIa), unstable angina (GPIIb/IIIa), restenosis (GPIIb/IIIa and integrin αvβ3), osteoporosis (αvβ3) and tumor metastasis (αvβ3). Antibodies and/or low-molecular weight compound antagonists of αvβ3 have shown efficacy against these respective disease states in animal models (J. Samanen, *Current Pharmaceutical Design*, 1997, 3, 545–584) and, thereby, offer promise as medicinal agents.

Antagonists of GPIIb/IIIa and αvβ3 have typically been designed after the bioactive arginine-glycine-aspartate (RGD) conformations of peptides derived from their primary ligands, fibrinogen and vitronectin, respectively. The RGD motif is the general cell attachment sequence of many extracellular matrices, blood and cell surface proteins, as half of approximately 20 known integrins bind the RGD-containing adhesion ligands. To discover RGD peptides with integrin selectivity, peptides with both restricted conformations and alterations of flanking residues have been studied. Iterative synthesis and computer modelling of these cyclic and alicyclic peptides have provided potent, selective agents as a platform for nonpeptide GPIIb/IIIa or αvβ3 antagonist design.

PCT Application WO 99/50249 describes guanidine-like compounds, unlike those of the present invention, as antagonists of αvβ3 and α2bβ3 integrin and related cell surface adhesive protein receptors.

PCT Application WO 01/10867 describes the use of benzazepine ethers and other compounds, unlike those of the present invention, as vitronectin antagonists for treating stroke and the post-traumatic injury associated with stroke.

Accordingly, it is an object of the present invention to provide quinazoline and quinazoline-like compounds that are integrin antagonists. It is an object of the invention to provide quinazoline and quinazoline-like compounds that are αvβ3, αvβ5, αvβ6 and GPIIb/IIIa integrin antagonists. It is also an object to provide a method for using a compound of the present invention for treating integrin-mediated disorders.

SUMMARY OF THE INVENTION

The present invention is directed to quinazoline and quinazoline-like compounds of Formula (I):

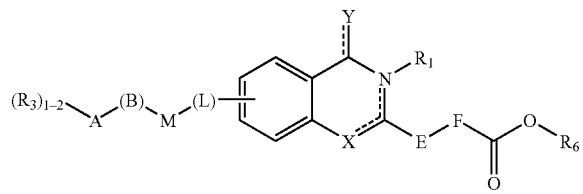

Formula (I)

wherein

A is selected from the group consisting of carbonyl, amino, carbamoyl, acetamido, acetimido, amidino, iminomethylamino, ureido, biureto, biurea, thioureido, guanidino, biguanido, biguanidino, amidrazone, hydrazo, carbazoyl, semicarbazido, cycloalkylene, heterocyclene, arylene and heteroarylene; wherein arylene and heteroarylene are optionally substituted with one to two additional substituents independently selected from the group consisting of $C_1$–$C_8$ alkyl, $C_1$–$C_8$ alkoxy, halogen, $(halo)_{1-3}(C_1$–$C_8)$ alkyl and $(halo)_{1-3}(C_1$–$C_8)$alkoxy;

(B) is optionally present and is selected from the group consisting of NH, O and C(O);

M is selected from the group consisting of $C_1$–$C_6$ alkylene, $C_2$–$C_6$ alkenylene, $C_2$–$C_6$ alkynylene and arylene; wherein arylene is optionally substituted with one to four additional substituents independently selected from the group consisting of $C_1$–$C_8$ alkyl, $C_1$–$C_8$ alkoxy, halogen, $(halo)_{1-3}(C_1$–$C_8)$alkyl and $(halo)_{1-3}(C_1$–$C_8)$alkoxy;

$R_3$ is one to two substituents independently selected from the group consisting of hydrogen, $C_1$–$C_8$ alkyl, cycloalkyl, heterocyclo, aryl, aryl($C_1$–$C_8$)alkyl, heteroaryl, heteroaryl($C_1$–$C_8$)alkyl, amino, $C_1$–$C_8$ alkylamino, di($C_1$–$C_8$)alkylamino, imino, iminomethyl, amidino, $C_1$–$C_8$ alkylamidino, di($C_1$–$C_8$)alkylamidino, cycloalkylamidino, halogen and hydroxy; wherein cycloalkyl, heterocyclo, aryl, heteroaryl and the aryl and heteroaryl portions of arylalkyl and heteroarylalkyl are optionally substituted with one to two substituents independently selected from the group consisting of $C_1$–$C_8$ alkyl, $C_1$–$C_8$ alkoxy, aryl and halogen; and, wherein heterocyclo is optionally substituted with a substituent selected from oxo;

(L) is optionally present and is selected from the group consisting of NH, O, S and C(O);

Y is selected from the group consisting of two substituents joined to the ring by single-bonds and one substituent joined to the ring by a double-bond; wherein the two substituents joined to the ring by single-bonds are independently selected from the group consisting of hydrogen, $C_1$–$C_8$ alkyl, $C_1$–$C_8$ alkoxy, halogen, $(halo)_{1-3}(C_1$–$C_4)$alkyl and $(halo)_{1-3}(C_1$–$C_4)$alkoxy; alternatively, the two substituents are taken together to form a moiety selected from the group consisting of cycloalkyl and —O—$(CH_2)_{1-4}$—O—; and, wherein the one substituent joined to the ring by a double-bond is selected from the group consisting of S, O, $C_1$–$C_8$ alkylidene, imino, $(C_1$–$C_4)$alkylimino, $(halo)_{1-2}$methylene and $(halo)_{1-3}(C_2$–$C_4)$alkylidene;

X is selected from the group consisting of N, NH, O and S;

$R_1$ is optionally present and is selected from the group consisting of hydrogen, $C_1$–$C_8$ alkyl, cycloalkyl, cycloalkyl($C_1$–$C_6$)alkyl, aryl, aryl($C_1$–$C_6$)alkyl, heteroaryl, heteroaryl($C_1$–$C_6$)alkyl, arylamino and heteroarylamino; wherein aryl, heteroaryl and the aryl and heteroaryl portions of arylalkyl and heteroarylalkyl are optionally substituted with one to five substituents independently selected from the group consisting of $C_1$–$C_8$ alkyl, $C_1$–$C_8$ alkoxy, aryl, aryl($C_1$–$C_8$)alkyl, heteroaryl, amino, $C_1$–$C_8$ alkylamino, di($C_1$–$C_8$ alkyl)amino, heteroarylamino, imino, iminomethyl, sulfonyl, halogen, hydroxy, nitro, cyano, (halo)$_{1-3}$($C_1$–$C_4$)alkyl and (halo)$_{1-3}$($C_1$–$C_4$)alkoxy;

E is $C_1$–$C_4$ alkyl substituted with W and W';

F is $C_1$–$C_4$ alkyl substituted with U and U';

W, W', U and U' are independently selected from the group consisting of hydrogen, $C_1$–$C_8$ alkyl, $C_2$–$C_8$ alkenyl, $C_2$–$C_8$ alkynyl, cycloalkyl, cycloalkyl($C_1$–$C_4$)alkyl, heterocyclo, heterocyclo($C_1$–$C_4$)alkyl, aryl, aryl($C_1$–$C_4$)alkyl, biaryl, heteroaryl, heteroaryl($C_1$–$C_4$)alkyl, —N[($R_4$),T($R_5$)] and halogen; wherein heterocyclo, aryl, biaryl, heteroaryl and the heterocyclo, aryl and heteroaryl portions of heterocycloalkyl, arylalkyl and heteroarylalkyl are optionally substituted with one to five substituents independently selected from the group consisting of $C_1$–$C_4$ alkyl, $C_1$–$C_4$ alkoxy, amino, $C_1$–$C_4$ alkylamino, di($C_1$–$C_4$ alkyl)amino, halogen, hydroxy, nitro and cyano; and, alternatively, two optional substituents on aryl, heteroaryl and the aryl and heteroaryl portions of arylalkyl and heteroarylalkyl are taken together to form a moiety selected from the group consisting of cycloalkyl, heterocyclo and —O—(CH$_2$)$_{1-4}$—O—; with the proviso that if one of W, W', U and U' are selected from —N[($R_4$),T($R_5$)], then the remaining W, W', U and U' cannot be selected from —N[($R_4$),T($R_5$)];

$R_4$ is selected from the group consisting of hydrogen and $C_1$–$C_8$ alkyl;

T is selected from the group consisting of arylene, carbonyl, carboxyl, sulfonyl and —C(O)NH—; wherein arylene is optionally substituted with one to two additional substituents independently selected from the group consisting of $C_1$–$C_4$ alkyl, $C_1$–$C_4$ alkoxy and halogen;

$R_5$ is selected from the group consisting of hydrogen, $C_1$–$C_8$ alkyl, $C_2$–$C_8$ alkenyl, cycloalkyl, heterocyclo, aryl, aryl($C_1$–$C_4$)alkyl, aryl($C_2$–$C_4$)alkenyl, biaryl, biaryl($C_1$–$C_4$) alkyl, heteroaryl, heteroaryl($C_1$–$C_4$)alkyl and amino; wherein heterocyclo, aryl, heteroaryl and the aryl and heteroaryl portions of arylalkyl, arylalkenyl, biaryl, biarylalkyl and heteroarylalkyl are optionally substituted with one to five substituents independently selected from the group consisting of $C_1$–$C_4$ alkyl, $C_1$–$C_4$ alkoxy, heterocyclo, aryl, aryl($C_1$–$C_4$)alkyl, arylsulfonyl, heteroaryl, amino, $C_1$–$C_4$ alkylamino, di($C_1$–$C_4$ alkyl)amino, halogen, hydroxy, (halo)$_{1-3}$($C_1$–$C_4$)alkyl and (halo)$_{1-3}$($C_1$–$C_4$) alkoxy; and, alternatively, two optional substituents on aryl, heteroaryl and the aryl and heteroaryl portions of arylalkyl, arylalkenyl and heteroarylalkyl are taken together to form a moiety selected from the group consisting of cycloalkyl, heterocyclo and —O—(CH$_2$)$_{1-4}$—O—;

$R_6$ is selected from the group consisting of hydrogen, $C_1$–$C_8$ alkyl and (CH$_2$)$_{1-8}$CON($R_7$)$_2$; and, $R_7$ is selected from the group consisting of hydrogen, $C_1$–$C_8$ alkyl and cycloalkyl;

and pharmaceutically acceptable racemates, enantiomers, diastereomers and salts thereof.

DETAILED DESCRIPTION OF THE INVENTION

Embodiments of the present invention include those compounds wherein, preferably, A is selected from the group consisting of carbonyl, amino, carbamoyl, amidino, iminomethylamino, ureido, guanidino, heterocyclene and heteroarylene; wherein heteroarylene is optionally substituted with one to two additional substituents independently selected from the group consisting of $C_1$–$C_4$ alkyl, $C_1$–$C_4$ alkoxy, halogen, (halo)$_{1-3}$($C_1$–$C_4$)alkyl and (halo)$_{1-3}$($C_1$–$C_4$) alkoxy.

More preferably, A is selected from the group consisting of amino, amidino, iminomethylamino, ureido, guanidino, heterocyclene and heteroarylene; wherein heteroarylene is optionally substituted with one to two additional substituents independently selected from the group consisting of $C_1$–$C_4$ alkyl, $C_1$–$C_4$ alkoxy, halogen, (halo)$_{1-3}$($C_1$–$C_4$)alkyl and (halo)$_{1-3}$($C_1$–$C_4$)alkoxy.

Most preferably, A is selected from the group consisting of amino, iminomethylamino, ureido, guanidino, pyrrolidinylene and pyridinylene; wherein pyridinylene is optionally substituted with one to two additional substituents independently selected from the group consisting of methyl, ethyl, n-propyl, i-propyl, n-butyl, t-butyl, methoxy, ethoxy, propoxy, chlorine, fluorine, bromine, trifluoromethyl and trifluoromethoxy.

Embodiments of the present invention include those compounds wherein, preferably, (B) is optionally present and is selected from the group consisting of O and C(O). More preferably, (B) is optionally present and is O.

Embodiments of the present invention include those compounds wherein, preferably, M is selected from the group consisting of —CH$_2$—, —(CH$_2$)$_2$—, —(CH$_2$)$_3$—, —(CH$_2$)$_4$—, —(CH$_2$)$_5$—, —C(CH$_3$)$_2$—, —CH(CH$_3$)—CH$_2$—, —CH$_2$—CH(CH$_3$)—, —CH(CH$_3$)—(CH$_2$)$_2$—, —(CH$_2$)$_2$—CH(CH$_3$)—, —C(CH$_3$)$_2$—CH$_2$—, —CH$_2$—C(CH$_3$)$_2$—, —CH=CH—, —CH=CH—CH$_2$—, —CH$_2$—CH=CH—, —CH$_2$—C(=CH$_2$)—, —CH=C(CH$_3$)—, —C(CH$_3$)=CH—, —CH=CH—(CH$_2$)$_2$—, —CH$_2$—CH=CH—CH$_2$—, —(CH$_2$)$_2$—CH=CH—, —CH(CH$_3$)—CH=CH—, —C≡C—, —C≡C—CH$_2$—, —CH$_2$—C≡C—, —C≡C—(CH$_2$)$_2$—, —(CH$_2$)$_2$—C≡C— and -Ph-; wherein phenylene is optionally substituted with one to four additional substituents independently selected from the group consisting of $C_1$–$C_4$ alkyl, $C_1$–$C_4$ alkoxy, halogen, (halo)$_{1-3}$($C_1$–$C_4$)alkyl and (halo)$_{1-3}$($C_1$–$C_4$)alkoxy.

More preferably, M is selected from the group consisting of —(CH$_2$)$_2$—, —(CH$_2$)$_3$—, —(CH$_2$)$_4$—, —C(CH$_3$)$_2$—, —CH(CH$_3$)—(CH$_2$)$_2$—, —C(CH$_3$)$_2$—CH$_2$—, —CH=CH—, —CH=CH—CH$_2$—, —CH$_2$—CH=CH—, —CH$_2$—C(=CH$_2$)—, —CH=C(CH$_3$)—, —C(CH$_3$)=CH—, —CH=CH—(CH$_2$)$_2$—, —CH$_2$—CH=CH—CH$_2$—, —(CH$_2$)$_2$—CH=CH—, —CH(CH$_3$)—CH=CH—, —C≡C—, —C≡C—CH$_2$—, —CH$_2$—C≡C—, —C≡C—(CH$_2$)$_2$—, —(CH$_2$)$_2$—C≡C— and -Ph-; wherein phenylene is optionally substituted with one to four additional substituents independently selected from the group consisting of $C_1$–$C_4$ alkyl, $C_1$–$C_4$ alkoxy, halogen, (halo)$_{1-3}$($C_1$–$C_4$)alkyl and (halo)$_{1-3}$($C_1$–$C_4$)alkoxy.

Most preferably, M is selected from the group consisting of —(CH$_2$)$_2$—, —(CH$_2$)$_3$—, —CH=CH—, —CH$_2$—CH=CH—, —CH$_2$—C(=CH$_2$)—, —CH=C(CH$_3$)—, —(CH$_2$)$_2$—CH=CH—, —C≡C—, —CH$_2$—C≡C—, —$(CH_2)_2$—C≡C— and -Ph-; wherein phenylene is optionally substituted with one to four additional substituents independently selected from the group consisting of methyl, ethyl, n-propyl, i-propyl, n-butyl, t-butyl, methoxy, ethoxy, propoxy, chlorine, fluorine, bromine, trifluoromethyl and trifluoromethoxy.

Embodiments of the present invention include those compounds wherein, preferably, $R_3$ is one to two substituents independently selected from the group consisting of hydrogen, $C_1$–$C_8$ alkyl, cycloalkyl, heterocyclo, aryl, aryl($C_1$–$C_8$) alkyl, heteroaryl, amino, ($C_1$–$C_8$ alkyl)amino, imino, amidino and halogen; wherein cycloalkyl and heteroaryl are optionally substituted with one to two substituents independently selected from the group consisting of $C_1$–$C_4$ alkyl, $C_1$–$C_4$ alkoxy and halogen; and, wherein heterocyclo is optionally substituted with a substituent selected from oxo.

More preferably, $R_3$ is one to two substituents independently selected from the group consisting of hydrogen, $C_1$–$C_4$ alkyl, cycloalkyl, heterocyclo, aryl, aryl($C_1$–$C_4$) alkyl, heteroaryl, amino, ($C_1$–$C_4$ alkyl)amino, imino and amidino; wherein cycloalkyl and heteroaryl are optionally substituted with one to two substituents independently selected from the group consisting of methyl, ethyl, n-propyl, i-propyl, n-butyl, t-butyl, methoxy, ethoxy, propoxy, chlorine, fluorine, bromine; and, wherein heterocyclo is optionally substituted with a substituent selected from oxo.

Most preferably, $R_3$ is one to two substituents independently selected from the group consisting of hydrogen, methyl, ethyl, n-propyl, i-propyl, n-butyl, cyclopropyl, cyclohexyl, 3,4-dihydro-2H-pyrrolyl, pyrrolidinyl, 4,5-dihydro-1H-imidazolyl, 3,4,5,6-tetrahydro-pyridinyl, 3,4-dihydro-quinazolinyl, 3,4,5,6-tetrahydro-2H-azepinyl, 3,4,5,6,7,8-hexahydro-azocinyl, phenyl, benzyl, phenethyl, oxazolyl, imidazolyl, pyridinyl, amino, methylamino, ethylamino, imino and amidino; wherein cyclopropyl, oxazolyl, imidazolyl and pyridinyl are optionally substituted with one to two substituents independently selected from the group consisting of methyl and chlorine; and, wherein 3,4-dihydro-quinazolinyl is optionally substituted with a substituent selected from oxo.

Embodiments of the present invention include those compounds wherein, preferably, (L) is optionally present and is O. More preferably, (L) is not present.

Embodiments of the present invention include those compounds wherein, preferably, Y is selected from the group consisting of two substituents joined to the ring by single-bonds and one substituent joined to the ring by a double-bond; wherein the two substituents joined to the ring by single-bonds are independently selected from the group consisting of hydrogen, $C_1$–$C_4$ alkyl, $C_1$–$C_4$ alkoxy, halogen, (halo)$_{1-3}$($C_1$–$C_4$)alkyl and (halo)$_{1-3}$($C_1$–$C_4$)alkoxy; and, wherein the one substituent joined to the ring by a double-bond is selected from the group consisting of S, O, $C_1$–$C_4$ alkylidene, imino, ($C_1$–$C_4$)alkylimino and (halo)$_2$methylene.

More preferably, Y is one substituent joined to the ring by a double-bond selected from the group consisting of S, O, methylene, ethylidene, imino, N-methylimino, N-ethylimino and difluoromethylene.

Most preferably, Y is one substituent joined to the ring by a double-bond selected from O.

Embodiments of the present invention include those compounds wherein, preferably, X is selected from the group consisting of N and NH. More preferably, X is N.

Embodiments of the present invention include those compounds wherein, preferably, $R_1$ is selected from the group consisting of hydrogen, $C_1$–$C_4$ alkyl, aryl and aryl($C_1$–$C_4$) alkyl; wherein aryl and the aryl portion of arylalkyl are optionally substituted with one to five substituents independently selected from the group consisting of $C_1$–$C_4$ alkyl, $C_1$–$C_4$ alkoxy, aryl, aryl($C_1$–$C_4$)alkyl, heteroaryl, amino, $C_1$–$C_4$ alkylamino, di($C_1$–$C_4$ alkyl)amino, heteroarylamino, imino, iminomethyl, sulfonyl, halogen, hydroxy, nitro, cyano, (halo)$_{1-3}$($C_1$–$C_4$)alkyl and (halo)$_{1-3}$($C_1$–$C_4$)alkoxy.

More preferably, $R_1$ is selected from the group consisting of hydrogen, methyl, ethyl, n-propyl, n-butyl, t-butyl, phenyl, naphthalenyl, benzyl and phenethyl. Most preferably, $R_1$ is selected from the group consisting of hydrogen, methyl, ethyl, n-propyl and benzyl.

Embodiments of the present invention include those compounds wherein, preferably, E is selected from the group consisting of —C(W,W')—, —C(W,W')—$CH_2$—, —CH(W)—CH(W')— and —$CH_2$—C(W,W')—. More preferably, E is selected from —C(W,W')—.

Embodiments of the present invention include those compounds wherein, preferably, F is selected from the group consisting of —C(U,U')—, —C(U,U')—$CH_2$—, —CH(U)—CH(U')— and —$CH_2$—C(U,U')—. More preferably, F is selected from the group consisting of —C(U,U')—$CH_2$— and —C(U,U')—. Most preferably, F is selected from —C(U,U')—.

Embodiments of the present invention include those compounds wherein, preferably, W, W', U and U' are independently selected from the group consisting of hydrogen, $C_1$–$C_4$ alkyl, $C_2$–$C_4$ alkenyl, $C_2$–$C_4$ alkynyl, heterocyclo, aryl, aryl($C_1$–$C_4$)alkyl, heteroaryl, —N[($R_4$),T($R_5$)] and halogen; wherein heterocyclo, aryl, heteroaryl and the aryl portion of arylalkyl are optionally substituted with one to five substituents independently selected from the group consisting of $C_1$–$C_4$ alkyl, $C_1$–$C_4$ alkoxy, amino, $C_1$–$C_4$ alkylamino, di($C_1$–$C_4$ alkyl)amino, halogen, hydroxy, nitro and cyano; and, alternatively, two optional substituents on aryl, heteroaryl and the aryl portion of arylalkyl are taken together to form a moiety selected from —O—$(CH_2)_{1-4}$—O—; with the proviso that if one of W, W', U and U' are selected from —N[($R_4$),T($R_5$)], then the remaining W, W', U and U' cannot be selected from —N[($R_4$),T($R_5$)].

More preferably, W, W', U and U' are independently selected from the group consisting of hydrogen, heterocyclo, aryl, aryl($C_1$–$C_4$)alkyl, heteroaryl and —N[($R_4$),T($R_5$)]; wherein aryl, heteroaryl and the aryl portion of arylalkyl are optionally substituted with one to five substituents independently selected from the group consisting of $C_1$–$C_4$ alkyl, $C_1$–$C_4$ alkoxy, halogen and hydroxy; and, alternatively, two optional substituents on aryl are taken together to form a moiety selected from —O—$(CH_2)_{1-4}$—O—; with the proviso that if one of W, W', U and U' are selected from —N[($R_4$),T($R_5$)], then the remaining W, W', U and U' cannot be selected from —N[($R_4$),T($R_5$)].

Most preferably, W, W', U and U' are independently selected from the group consisting of hydrogen and —N[($R_4$),T($R_5$)]; with the proviso that if one of W, W', U and U' are selected from —N[($R_4$),T($R_5$)], then the remaining W, W', U and U' cannot be selected from —N[($R_4$),T($R_5$)].

Embodiments of the present invention include those compounds wherein, preferably, $R_4$ is selected from the group consisting of hydrogen and $C_1$–$C_4$ alkyl. More preferably, $R_4$ is selected from the group consisting of hydrogen, methyl, ethyl, n-propyl, i-propyl, n-butyl and t-butyl. Most preferably, $R_4$ is hydrogen.

Embodiments of the present invention include those compounds wherein, preferably, T is selected from the group consisting of carbonyl, carboxyl, sulfonyl and —C(O)

NH—. More preferably, T is selected from the group consisting of carboxyl, sulfonyl and —C(O)NH—.

Embodiments of the present invention include those compounds wherein, preferably, $R_5$ is selected from the group consisting of hydrogen, $C_1$–$C_4$ alkyl, $C_2$–$C_4$ alkenyl, aryl, aryl($C_1$–$C_4$)alkyl, aryl($C_2$–$C_4$)alkenyl, heteroaryl and amino; wherein aryl, heteroaryl and the aryl portion of arylalkyl and arylalkenyl are optionally substituted with one to five substituents independently selected from the group consisting of $C_1$–$C_4$ alkyl, $C_1$–$C_4$ alkoxy, arylsulfonyl, heteroaryl, di($C_1$–$C_4$ alkyl)amino, halogen, trifluoro($C_1$–$C_4$) alkyl and trifluoro($C_1$–$C_4$)alkoxy; and, alternatively, two optional substituents on aryl and the aryl portion of arylalkyl and arylalkenyl are taken together to form a moiety selected from —O—$(CH_2)_{1-4}$—O—.

More preferably, $R_5$ is selected from the group consisting of methyl, ethyl, n-propyl, i-propyl, n-butyl, t-butyl, ethenyl, propenyl, phenyl, naphthalenyl, benzyl, naphthalenethyl, phenethenyl, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, quinolinyl, isoquinolinyl and amino; wherein phenyl, naphthalenyl, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, quinolinyl, isoquinolinyl and the phenyl portion of benzyl and phenethenyl are optionally substituted with one to five substituents independently selected from the group consisting of methyl, ethyl, i-propyl, n-propyl, n-butyl, t-butyl, methoxy, ethoxy, propoxy, phenylsulfonyl, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, N,N-dimethylamino, N,N-diethylamino, chlorine, fluorine, trifluoromethyl and trifluoromethoxy; and, alternatively, two optional substituents on phenyl and the phenyl portion of benzyl and phenethenyl are taken together to form a moiety selected from —O—$(CH_2)_{1-4}$—O—.

Most preferably, $R_5$ is selected from the group consisting of n-butyl, t-butyl, phenyl, naphthalenyl, benzyl, naphthalenethyl, phenethenyl, thienyl, pyrazolyl, isoxazolyl and quinolinyl; wherein phenyl, naphthalenyl, thienyl, pyrazolyl, isoxazolyl and the phenyl portion of benzyl and phenethenyl are optionally substituted with one to five substituents independently selected from the group consisting of methyl, t-butyl, methoxy, phenylsulfonyl, isoxazolyl, pyridinyl, N,N-dimethylamino, chlorine, trifluoromethyl and trifluoromethoxy; and, alternatively, two optional substituents on phenyl and the phenyl portion of benzyl and phenethenyl are taken together to form a moiety selected from —O—$(CH_2)$—O—.

Embodiments of the present invention include those compounds wherein, preferably, $R_6$ is selected from the group consisting of hydrogen, $C_1$–$C_4$ alkyl and $(CH_2)_{1-4}$CON$(R_7)_2$. More preferably, $R_6$ is selected from the group consisting of hydrogen, methyl, ethyl, n-propyl and $CH_2$CON$(R_7)_2$. Most preferably, $R_6$ is selected from the group consisting of hydrogen and methyl.

Embodiments of the present invention include those compounds wherein, preferably, $R_7$ is selected from the group consisting of hydrogen and $C_1$–$C_4$ alkyl. More preferably, $R_7$ is selected from the group consisting of hydrogen and methyl.

Embodiments of the present invention include those compounds of Formula (Ia) shown in Table 1.

TABLE 1

Formula (Ia)

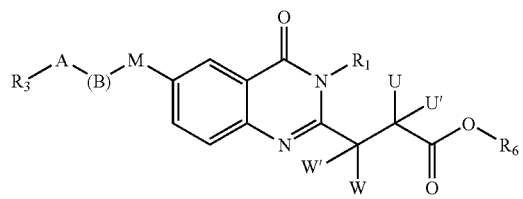

wherein $R_3$, A, (B), M, W, W', U, U', $R_1$ and $R_6$ are dependently selected from the group consisting of

| Cpd | $R_3$ | A | (B) | M | W, W' | U, U' | $R_1$ | $R_6$ |
|---|---|---|---|---|---|---|---|---|
| 1 | 4,5-dihydro-1H-imidazol-2-yl | NH | — | $CH_2(CH)_2$ | H, H | $(Me_5)Ph$ $SO_2NH$, H | H | H; |
| 1a | 4,5-dihydro-1H-imidazol-2-yl | NH | — | $CH_2(CH)_2$ | H, H | $(Me_5)Ph$ $SO_2NH$, H | H | Na; |
| 2 | 4,5-dihydro-1H-imidazol-2-yl | NH | — | $CH_2(CH)_2$ | H, H | $PhCH_2OC(O)NH$, H | H | H; |
| 3 | 4,5-dihydro-1H-imidazol-2-yl | NH | — | $CH_2(CH)_2$ | H, H | $2,4,6-Me_3Ph$ $SO_2NH$, H | H | H; |
| 4 | 4,5-dihydro-1H-imidazol-2-yl | NH | — | $CH_2(CH)_2$ | H, H | 8-quinolinyl $SO_2NH$, H | H | H; |
| 5 | 4,5-dihydro-1H-imidazol-2-yl | NH | — | $CH_2(CH)_2$ | H, H | 1-naphthalenyl$(CH_2)_2$ $SO_2NH$, H | H | H; |
| 6 | 4,5-dihydro-1H-imidazol-2-yl | NH | — | $CH_2(CH)_2$ | H, H | 5-(2-pyridinyl)-2-thienyl $SO_2NH$, H | H | H; |

TABLE 1-continued

Formula (Ia)

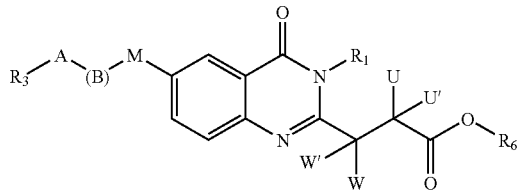

wherein $R_3$, A, (B), M, W, W', U, U', $R_1$ and $R_6$ are dependently selected from the group consisting of

| Cpd | $R_3$ | A | (B) | M | W, W' | U, U' | $R_1$ | $R_6$ |
|---|---|---|---|---|---|---|---|---|
| 7 | 4,5-dihydro-1H-imidazol-2-yl | NH | — | $CH_2(CH_2)_2$ | H, H | $PhCH_2SO_2NH$, H | H | H; |
| 8 | 4,5-dihydro-1H-imidazol-2-yl | NH | — | $(CH_2)_2(CH_2)_2$ | H, H | $PhCH_2OC(O)NH$, H | H | H; |
| 9 | 4,5-dihydro-1H-imidazol-2-yl | NH | — | 3-Ph | H, H | $PhCH_2OC(O)NH$, H | H | H; |
| 10 | 2-pyridinyl | NH | — | $CH_2(CH_2)_2$ | H, H | $(Me_5)PhSO_2NH$, H | H | H; |
| 11 | 2-pyridinyl | NH | — | $(CH_2)_3$ | H, H | $(Me_5)PhSO_2NH$, H | H | H; |
| 12 | 2-pyridinyl | NH | — | $CH_2(CH_2)_2$ | H, H | $PhNHC(O)NH$, H | H | H; |
| 13 | Ph | NHC(O)NH | — | $CH_2(CH_2)_2$ | H, H | $(Me_5)PhSO_2NH$, H | H | H; |
| 14 | 2-pyridinyl | NH | — | $CH_2(CH_2)_2$ | $(Me_5)PhSO_2NH$, H | H, H | H | H; |
| 15 | 3,4-dihydro-2H-pyrrol-5-yl | NH | — | $CH_2(CH_2)_2$ | H, H | $(Me_5)PhSO_2NH$, H | H | H; |
| 16 | — | $NH_2C(NH)NH$ | O | $(CH_2)_2(CH_2)_2$ | H, H | $(Me_5)PhSO_2NH$, H | H | H; |
| 17 | 2-pyridinyl | NH | — | $CH_2(CH_2)_2$ | 3-MeOPh, H | H, H | H | H |
| 18 | 2-pyridinyl | NH | — | $CH_2(CH_2)_2$ | 3-MeOPh, H | H, H | $CH_3$ | H |
| 19 | H | NH | — | $CH_2(CH_2)_2$ | H, H | $PhCH_2OC(O)NH$, H | H | H; |
| 20 | 4,5-dihydro-1H-imidazol-2-yl | NH | — | $CH_2(C)_2$ | H, H | $PhCH_2OC(O)NH$, H | H | H; |
| 21 | 4,5-dihydro-1H-imidazol-2-yl | NH | — | $CH_2(CH_2)_2$ | H, H | $2,4,6-Cl_3PhSO_2NH$, H | H | H; |
| 22 | 4,5-dihydro-1H-imidazol-2-yl | NH | — | $CH_2(CH_2)_2$ | H, H | 5-$(Me_2N)$-1-naphthalenyl $SO_2NH$, H | H | H; |
| 23 | 2-pyridinyl | NH | — | $CH_2(CH_2)_2$ | H, H | 4-(t-butyl)Ph $SO_2NH$, H | H | H; |
| 24 | 2-pyridinyl | NH | — | $CH_2(CH_2)_2$ | H, H | 2-naphthalenyl $SO_2NH$, H | H | H; |
| 25 | 2-pyridinyl | NH | — | $CH_2(CH_2)_2$ | H, H | $4-F_3MePhSO_2NH$, H | H | H; |
| 26 | 2-pyridinyl | NH | — | $CH_2(CH_2)_2$ | H, H | $4-MeOPhSO_2NH$, H | H | H; |
| 27 | 2-imino | 1-pyrrolidinyl | — | $CH_2(CH_2)_2$ | H, H | $(Me_5)PhSO_2NH$, H | H | H; |
| 28 | 2-pyridinyl | NH | — | $CH_2(CH_2)_2$ | H, H | 5-$(PhSO_2)$-2-thienyl $SO_2NH$, H | H | H; |
| 29 | 2-pyridinyl | NH | — | $CH_2(CH_2)_2$ | H, H | 2-Cl-6-MePh $SO_2NH$, H | H | H; |
| 30 | 1-Me-1H-imidazol-2-yl | NH | — | $CH_2(CH_2)_2$ | H, H | $(Me_5)PhSO_2NH$, H | H | H; |
| 31 | 2-pyridinyl | NH | — | $CH_2(CH_2)_2$ | H, H | 5-(3-isoxazolyl)-2-thienyl $SO_2NH$, H | H | H; |

TABLE 1-continued

Formula (Ia)

$$\text{structure with } R_3\text{-A-(B)-M-[quinazolinone core with } R_1\text{]-C(W)(W')-C(U)(U')-C(O)-O-R_6$$

wherein $R_3$, A, (B), M, W, W', U, U', $R_1$ and $R_6$ are dependently selected from the group consisting of

| Cpd | $R_3$ | A | (B) | M | W, W' | U, U' | $R_1$ | $R_6$ |
|---|---|---|---|---|---|---|---|---|
| 32 | 2-pyridinyl | NH | — | CH$_2$ (CH$_2$) | H, H | 2,5-(MeO)$_2$Ph SO$_2$NH, H | H | H; |
| 33 | 2-pyridinyl | NH | — | CH$_2$ (CH$_2$) | H, H | 3,4-(MeO)$_2$Ph SO$_2$NH, H | H | H; |
| 34 | 2-pyridinyl | NH | — | CH$_2$ (CH$_2$) | H, H | 2-thienyl SO$_2$NH, H | H | H; |
| 35 | 2-pyridinyl | NH | — | CH$_2$ (CH$_2$) | H, H | 4-F$_3$MeOPh SO$_2$NH, H | H | H; |
| 36 | 2-pyridinyl | NH | — | CH$_2$ (CH$_2$) | H, H | 5-Cl-1,3-Me$_2$-1H-pyrazol-4-yl SO$_2$NH, H | H | H; |
| 37 | 2-pyridinyl | NH | — | CH$_2$ (CH$_2$) | H, H | 3,5-Me$_2$-4-isoxazoyl SO$_2$NH, H | H | H; |
| 38 | 3-Me-2-pyridinyl | NH | — | CH$_2$ (CH$_2$) | H, H | (Me$_5$)Ph SO$_2$NH, H | H | H; |
| 39 | 5-Cl-2-pyridinyl | NH | — | CH$_2$ (CH$_2$) | H, H | (Me$_5$)Ph SO$_2$NH, H | H | H; |
| 40 | 5-Cl-2-pyridinyl | NH | — | CH$_2$ (CH$_2$) | H, H | 4-MeOPh SO$_2$NH, H | H | H; |
| 41 | 4,5-dihydro-1H-imidazol-2-yl | NH | — | CH$_2$ (CH$_2$) | H, H | (Me$_5$)Ph SO$_2$NH, H | H | CH$_3$; |
| 42 | 4,5-dihydro-1H-imidazol-2-yl | NH | — | (CH$_2$)$_2$ (CH$_2$) | H, H | (Me$_5$)Ph SO$_2$NH, H | H | H; |
| 43 | 5-Me-2-pyridinyl | NH | — | CH$_2$ (CH$_2$) | H, H | (Me$_5$)Ph SO$_2$NH, H | H | H; |
| 44 | 5-Me-2-pyridinyl | NH | — | CH$_2$ (CH$_2$) | H, H | 3,4-(MeO)$_2$Ph SO$_2$NH, H | H | H; |
| 45 | 4-Me-2-pyridinyl | NH | — | CH$_2$ (CH$_2$) | H, H | (Me$_5$)Ph SO$_2$NH, H | H | H; |
| 46 | 4-Me-2-pyridinyl | NH | — | CH$_2$ (CH$_2$) | H, H | 3,4-(MeO)$_2$Ph SO$_2$NH, H | H | H; |
| 47 | 3-pyridinyl | C(NH) NH | — | CH$_2$ (CH$_2$) | H, H | (Me$_5$)Ph SO$_2$NH, H | H | H; |
| 48 | 4,5-dihydro-1H-imidazol-2-yl | NH | — | CH$_2$ (CH$_2$) | H, H | 3,4-(MeO)$_2$Ph SO$_2$NH, H | H | H; |
| 49 | benzyl | NH C(O)NH | — | CH$_2$ (CH$_2$) | H, H | (Me$_5$)Ph SO$_2$NH, H | H | H; |
| 50 | 4,5-dihydro-1H-imidazol-2-yl | NH | — | CH$_2$ (CH$_2$) | H, H | 4-MeOPh SO$_2$NH, H | H | H; |
| 51 | n-butyl | NH C(O)NH | — | CH$_2$ (CH$_2$) | H, H | (Me$_5$)Ph SO$_2$NH, H | H | H; |
| 52 | 3,4,5,6-tetrahydro-2-pyridinyl | NH | — | CH$_2$ (CH$_2$) | H, H | (Me$_5$)Ph SO$_2$NH, H | H | H; |
| 53 | — | NH$_2$ C(O)NH | — | CH$_2$ (CH$_2$) | H, H | (Me$_5$)Ph SO$_2$NH, H | H | H; |
| 54 | benzyl | NH C(O)NH | — | CH$_2$ (CH$_2$) | H, H | 3,4-(MeO)$_2$Ph SO$_2$NH, H | H | H; |
| 55 | 3,4-dihydro-2H-pyrrol-5-yl | NH | — | CH$_2$ (CH$_2$) | H, H | 3,4-(MeO)$_2$Ph SO$_2$NH, H | H | H; |

TABLE 1-continued

Formula (Ia)

$$\text{R}_3\text{-A-(B)-M-[quinazolinone core with R}_1\text{, U, U', W, W', C(O)OR}_6\text{]}$$

wherein R₃, A, (B), M, W, W', U, U', R₁ and R₆ are dependently selected from the group consisting of

| Cpd | R₃ | A | (B) | M | W, W' | U, U' | R₁ | R₆ |
|---|---|---|---|---|---|---|---|---|
| 56 | benzyl | NH C(O)NH | — | CH₂ (CH₂) | H, H | 4-MeO-2,3,6-Me₃Ph SO₂NH, H | H | H; |
| 57 | benzyl | NH C(O)NH | — | CH₂ (CH₂) | H, H | 4-MeOPh SO₂NH, H | H | H; |
| 58 | i-propyl | NH C(O)NH | — | CH₂ (CH₂) | H, H | (Me₅)Ph SO₂NH, H | H | H; |
| 59 | methyl | NH C(O)NH | — | CH₂ (CH₂) | H, H | (Me₅)Ph SO₂NH, H | H | H; |
| 60 | 3,4,5,6-tetrahydro-2-pyridinyl | NH | — | CH₂ (CH₂) | H, H | 3,4-(MeO)₂Ph SO₂NH, H | H | H; |
| 61 | 3,4-dihydro-4-oxo-2-quinazolinyl | NH | — | CH₂ (CH₂) | H, H | (Me₅)Ph SO₂NH, H | H | H; |
| 62 | benzyl | NH C(O)NH | — | CH₂ (CH₂) | H, H | 2,4,6-Me₃Ph SO₂NH, H | H | H; |
| 63 | 4,5-dihydro-1H-imidazol-2-yl | NH | — | CH₂ (CH₂) | H, H | 4-MeO PhOC(O)NH, H | H | H; |
| 64 | i-propyl | NH C(O)NH | — | CH₂C (CH₂) | H, H | (Me₅)Ph SO₂NH, H | H | H; |
| 65 | benzyl | NH C(O)NH | — | CH₂ (CH₂) | H, H | 5-Cl-1,3-Me₂-1H-pyrazol-4-yl SO₂NH, H | H | H; |
| 66 | 2-Ph cyclopropyl | NH C(O)NH | — | CH₂ (CH₂) | H, H | (Me₅)Ph SO₂NH, H | H | H; |
| 67 | 3,4-dihydro-2H-pyrrol-5-yl | NH | — | CH₂ (CH₂) | H, H | PhCH₂OC(O)NH, H | H | H; |
| 68 | 3,4,5,6,7,8-hexahydro-2-azocinyl | NH | — | CH₂ (CH₂) | H, H | 3,4-(MeO)₂Ph SO₂NH, H | H | H; |
| 69 | 4-Me-2-pyridinyl | NH | — | CH₂ (CH₂) | H, H | PhCH₂OC(O)NH, H | H | H; |
| 70 | benzyl | NH C(O)NH | — | CH₂ (CH₂) | H, H | PhCH₂ SO₂NH, H | H | H; |
| 71 | 3,4,5,6-tetrahydro-2H-azepin-7-yl | NH | — | CH₂ (CH₂) | H, H | (CH₃)₃COC(O)NH, H | H | H; |
| 72 | benzyl | NH C(O)NH | — | CH₂ (CH₂) | H, H | 2-thienyl SO₂NH, H | H | H; |
| 73 | benzyl | NH C(O)NH | — | CH₂ (CH₂) | H, H | n-butyl SO₂NH, H | H | H; |
| 74 | 3,4,5,6-tetrahydro-2H-azepin-7-yl | NH | — | CH₂ (CH₂) | H, H | (Me₅)Ph SO₂NH, H | H | H; |
| 75 | cyclohexyl | NH C(O)NH | — | CH₂ (CH₂) | H, H | (Me₅)Ph SO₂NH, H | H | H; |
| 76 | benzyl | NH C(O)NH | — | CH₂ (CH₂) | H, H | 1-naphthalenyl(CH₂)₂ SO₂NH, H | H | H; |
| 77 | benzyl | NH C(O)NH | — | CH₂ (CH₂) | H, H | 4-MeO PhOC(O)NH, H | H | H; |
| 78 | 4,5-dihydro-1H-imidazol-2-yl | NH | — | CH₂ (CH₂) | Ph, H | H, H | CH₃ | H; |

TABLE 1-continued

Formula (Ia)

wherein $R_3$, A, (B), M, W, W', U, U', $R_1$ and $R_6$ are dependently selected from the group consisting of

| Cpd | $R_3$ | A | (B) | M | W, W' | U, U' | $R_1$ | $R_6$ |
|---|---|---|---|---|---|---|---|---|
| 79 | cyclohexyl | NHC(O)NH | — | CHC(CH$_3$) | H, H | (Me$_5$)PhSO$_2$NH, H | H | H; |
| 80 | phenethyl | NHC(O)NH | — | CH$_2$(CH)$_2$ | H, H | (Me$_5$)PhSO$_2$NH, H | H | H; |
| 81 | 4-Me-2-oxazolyl | NH | — | CH$_2$(CH)$_2$ | H, H | (Me$_5$)PhSO$_2$NH, H | H | H; |
| and |  |  |  |  |  |  |  |  |
| 82 | 2-pyridinyl | NH | — | CH$_2$(CH)$_2$ | H, H | H, H | PhCH$_2$ | H; | and pharmaceutically acceptable racemates, enantiomers, diastereomers and salts thereof.

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. Pharmaceutically acceptable salts may take a form in which a nitrogen on a guanidine or amidine surrogate substituent is protonated with an inorganic or organic acid. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid.

Pharmaceutically acceptable salts for compounds of the present invention may also take a form in which a hydrogen on the carboxylic acid is deprotonated and replaced with an alkali metal cation (sodium, lithium or potassium), an alkaline earth metal cation (calcium or magnesium) or other pharmaceutically acceptable inorganic or organic cations such as an ammonium cation.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

The compounds according to this invention may have at least one chiral center and thus may exist as enantiomers. In addition, the compounds of the present invention may also possess two or more chiral centers and thus may also exist as diastereomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active acid, such as (–)-di-p-toluoyl-d-tartaric acid and/or (+)-di-p-toluoyl-ltartaric acid followed by fractional crystallization and regeneration of the free base. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, "alkyl" whether used alone or as part of a substituent group refers to straight and branched carbon chains having 1 to 8 carbon atoms or any number within this range. The term "alkoxy" refers to an —O-alkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain.

The term "cycloalkyl" refers to branched or unbranched cyclic aliphatic hydrocarbon chains of 3 to 8 carbon atom members. Examples of such cyclic alkyl rings include cyclopropyl, cyclobutyl, cyclopentyl, cyclohexyl or cycloheptyl.

The term "heterocyclo" refers to a nonaromatic cyclic ring of 5 to 8 members in which 1 to 4 members are nitrogen or a nonaromatic cyclic ring of 5 to 8 members in which zero, one or two members are nitrogen and one member is oxygen or sulfur; wherein, optionally, the ring contains zero, one or two unsaturated bonds. Optionally, the heterocyclo ring is fused to a benzene ring, a 5 or 6 membered heteroaryl ring (containing one of O, S or N and, optionally, one additional nitrogen), a 5 to 7 membered alicyclic ring or a 5 to 7 membered heterocyclo ring (of the same definition as above but absent the option of a further fused ring). For instant compounds of the invention, the carbon atom ring members that form the heterocyclo ring are fully saturated. Other compounds of the invention may have a partially saturated heterocyclo ring. Preferred partially saturated heterocyclo rings may have one or two double bonds. Such compounds are not considered to be fully aromatic and are not to be referred to as heteroaryl compounds. Examples of heterocyclo groups include pyrrolinyl (including 2H-pyrrole, 3,4-dihydro-2H-pyrrolyl, 2-pyrrolinyl or 3-pyrrolinyl), pyrrolidinyl, 2-imidazolinyl (including 4,5-dihydro-1H-imidazolinyl), imidazolidinyl, 2-pyrazolinyl, pyrazolidinyl, 3,4,5,6-tetrahydro-pyridinyl, piperidinyl, morpholinyl, thiomorpholinyl, piperazinyl, 3,4-dihydro-quinazolinyl, 3,4,5,6-tetrahydro-2H-azepinyl and 3,4,5,6,7,8-hexahydro-azocinyl.

The term "aryl" refers to a single aromatic ring of 6 carbon members or a bicyclic aromatic ring of 10 carbon members. Examples of such aryl rings include phenyl and naphthyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to two additional nitrogens. In the case of 6 membered rings, the heteroaryl ring may contain from one to three nitrogen atoms. For the case wherein the 6 member ring has three nitrogens, at most two nitrogen atoms are adjacent. Optionally, the heteroaryl ring is fused to a benzene ring, a 5 or 6 membered heteroaryl ring (containing one of O, S or N and, optionally, one additional nitrogen), a 5 to 7 membered alicyclic ring or a 5 to 7 membered heterocyclo ring (as defined supra but absent the option of a further fused ring). Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The terms "alkylene," "alkenylene," "alkynylene," "cycloalkylene," "heterocyclene," "arylene" and "heteroarylene" refer to alkyl, alkenyl, alkynyl, cycloalkyl, heterocyclo, aryl and heteroaryl linking groups, wherein alkyl, alkenyl, alkynyl, cycloalkyl, heterocyclo, aryl and heteroaryl are as defined supra.

The following terms, when used herein to define moieties that act as linking groups have the following meanings: "carbonyl" refers to —C(O)—, "amino" refers to —NH—, "carbamoyl" refers to —NHC(O)—, "acetamido" refers to —CH$_2$C(O)NH—, "acetimido" refers to —CH$_2$C(NH)—, "amidino" refers to —NHC(NH)—, "iminomethylamino" refers to —C(NH)NH—, "ureido" refers to —NHC(O)NH—, "biureto" refers to —HNC(O)NHC(O)NH—, "biurea" refers to —NHC(O)NHNHC(O)NH—, "gaunidino" refers to —NHC(NH)NH—, "biguanido" refers to —HN—C(NH)NHC(NH)NH—, and "biguanidino" refers to —HNC(NH)NHNHC(NH)NH—, "amidrazone" refers to —NHC(NH)NHNH— and "semicarbazido" refers to —NHC(O)NHNH—. As shown herein, the moieties for the variable A linking group are substituted with R$_3$ attached to the left portion of the moiety (in place of H) and with (B) (when present) or M attached to the right portion of the moiety. The term carbamoyl also refers to the moiety —C(O)NH— and, as shown herein for the variable T linking group, —C(O)NH— is substituted with R$_5$ attached to the right portion of the moiety (in place of H) and N of N(R$_4$) attached to the left portion of the moiety. When used to refer to a substituent for other portions of the compound, the moieties have a hydrogen attached to the left portion of the moiety, with the point of attachment on the right portion of the moiety.

As used herein, the term "carboxyl" refers to the linking group —C(O)O— or (when used accordingly) to the substituent —COOH; the term "imino" refers to the substituent HN= and the term "iminomethyl" refers to the substituent CH(NH)—.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., C$_1$–C$_6$) shall refer independently to the number of carbon atoms in an alkyl moiety or to the alkyl portion of a larger substituent in which alkyl appears as its prefix root. The amount of substituents attached to a moiety "optionally substituted with one to five substituents" is limited to that amount of open valences on the moiety available for substitution.

In general, under standard nomenclature rules used throughout this disclosure, the terminal portion of the designated side chain is described first followed by the adjacent functionality toward the point of attachment. Thus, for example, a "phenylC$_1$–C$_6$ alkylamidoC$_1$–C$_6$alkyl" substituent refers to a group of the formula:

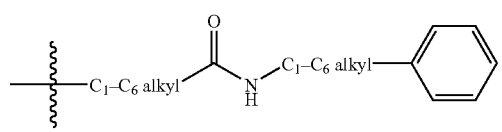

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The quinazoline and quinazoline-like compounds of the present invention are useful integrin antagonists (in particular, αvβ3, αvβ5, αvβ6, and GPIIb/IIIa integrin antagonists), inhibiting the binding of the adhesive blood proteins fibrinogen, fibronectin, vitronectin and osteopontin to the integrin class of receptors. Accordingly, the compounds of the present invention are useful for treating integrin-mediated disorders including, but not limited to, vaso-occlusive, angiogenic, inflammation and bone degradation disorders, including disorders associated with diabetes, cell apoptosis and tumor metastasis. More particularly, integrin-mediated disorders includes, and is not limited to, arterial thrombosis, venous thrombosis, acute myocardial infarction, re-occlusion following thrombolytic therapy, re-occlusion following angioplasty, unstable angina, restenosis, atherosclerosis, disorders mediated by angiogenesis (including vaso-occlusive disorders and proliferative diseases), inflammation, arthritis, bone resorption disorders (including osteoporosis), cancer, tumor metastasis, acute renal failure, macular degeneration, diabetic complications (including diabetic retinopathy and phagocytosis of cells undergoing apoptosis), stroke and the post-traumatic injury associated with stroke.

These compounds are also useful antithrombotics when used in conjunction with fibrinolytic therapy (e.g., t-PA or streptokinase). Additionally, the compounds are useful for the treatment and prevention of inflammation, arthritis, osteoporosis and for treating bone resorption disorders, cancer, macular degeneration and diabetic complications including retinopathy. Administration of the instant compounds are useful in decreasing total infarction volume following stroke, in preventing additional strokes and in treating the post-traumatic injury associated with stroke. When used for treating and/or preventing osteoporosis or bone resorption, the compounds of the present invention may be administered in combination with a bone resorption inhibitor; preferably, the bone resorption inhibitor is alendronate or may be used in combination with one or more agents useful in the prevention or treatment of osteoporosis and arthritis. For example, the compounds of the instant invention may be effectively administered in combination with other agents used in the treatment of osteoporosis such as bisphosphonate bone resorption inhibitors; preferably, the bisphosphonate bone resorption inhibitor is alendronate, sold as FOSAMAX®. Preferred combinations are simultaneous or alternating treatments of an integrin antagonist of the present invention and alendronate.

Illustrative of the invention is a pharmaceutical composition comprising a pharmaceutically acceptable carrier and any of the compounds described above. Also illustrative of the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier. The present invention also provides pharmaceutical compositions comprising one or more compounds of this invention in association with a pharmaceutically acceptable carrier.

An embodiment of the invention is a method for treating integrin-mediated disorders in a subject in need thereof comprising administering to the subject a therapeutically effective amount of any of the compounds or pharmaceutical compositions described above. Also included in the invention is the use of a compound of Formula (I) for the preparation of a medicament for treating an integrin-mediated disorder in a subject in need thereof. The term "treating" as used herein refers to a method for improving, halting, retarding or palliating an integrin mediated disorder in the subject in need thereof. All such methods of treatment are intended to be within the scope of the present invention.

In accordance with the methods of the present invention, the individual components of the pharmaceutical compositions described herein can be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The term "bone resorption," as used herein, refers to the process by which osteoclasts degrade bone.

As used herein, the term "composition" is intended to encompass a product comprising the specified ingredients in the specified amounts, as well as any product which results, directly or indirectly, from combinations of the specified ingredients in the specified amounts.

The utility of the compounds to treat integrin-mediated disorders can be determined according to the procedures herein. The present invention therefore provides a method for the treatment of integrin-mediated disorders in a subject in need thereof which comprises administering any of the compounds as defined herein in a quantity effective to treat vaso-occlusive disorders and proliferative diseases mediated by angiogenesis, inflammation and bone resorption disorders, cell apoptosis and tumor metastasis and diabetic complications. A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1–3, edited by Lieberman et al; *Pharmaceutical Dosage Forms: Parenteral Medications*, Volumes 1–2, edited by Avis et al; and *Pharmaceutical*

*Dosage Forms: Disperse Systems*, Volumes 1–2, edited by Lieberman et al; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to accacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c)dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phophatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treatment of integrin-mediated disorders is required for a subject in need thereof.

The therapeutically effective amount of a compound or pharmaceutical composition thereof may be from about 0.01 mg/Kg/dose to about 300 mg/Kg/dose. Preferably, the therapeutically effective amount may be from about 0.01 mg/Kg/dose to about 100 mg/Kg/dose. More preferably, the therapeutically effective amount may be from about 0.01 mg/Kg/dose to about 50 mg/Kg/dose. Most preferably, the therapeutically effective amount may be from about 0.01 mg/Kg/dose to about 30 mg/Kg/dose. Therefore, the therapeutically effective amount of the active ingredient contained per dosage unit (e.g., tablet, capsule, powder, injection, suppository, teaspoonful and the like) as described herein will be in the range of from about 1 mg/day to about 21,000 mg/day for a subject, for example, having an average weight of 70 Kg. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. Advantageously, compounds of the present invention may be administered in a single daily dose or the total daily dosage may be administered in divided doses of two, three or four times daily.

Abbreviations used in the instant specification, particularly the Schemes and Examples, are as follows:
Bn or Bzl=benzyl
Boc=tert-butoxycarbonyl
BSA=bovine serum albumin
CBZ=benzyloxycarbonyl
CP=compound
DCM=dichloromethane
DEAD=diethyl azodicarboxylate
DIPEA=diisopropylethylamine
DMAP=4-dimethylaminopyridine
DMF=N,N-dimethylformamide
DMSO=dimethylsulfoxide
EDC=ethyl dimethylaminopropyl-carbodiimide
EDTA=ethylenediaminetetraacetic acid
$Et_3N$=triethylamine
$Et_2O$=diethyl ether
EtOH=ethanol
Hrs=hours
HEPES=4-(2-hydroxyethyl)-1-piperazine-ethanesulfonic acid
Me=methyl
MeCN=acetonitrile
MeOH=methanol
MPK=milligrams per kilogram
NMM=N-methylmorpholine
NT=not tested
(o-tolyl)$_3$P=tri-o-tolylphosphine
Pd/C=palladium on activated carbon
Pd(OAc)$_2$=palladium(II) acetate
Ph=phenyl
Ph$_3$P=triphenylphosphine
PPT=precipitate
RT=room temperature
TEA=triethylamine
THF=tetrahydrofuran
TFA=trifluoroacetic acid
TMS=tretramethylsilane
TMSCHN$_2$=trimethylsilyldiazomethane
Z=benzyloxycarbonyl General Synthetic Methods Representative compounds of the present invention can be synthesized in accordance with the general synthetic methods described below and are illustrated more particularly in the scheme that follows. Since the scheme is an illustration, the invention should not be construed as being limited by the chemical reactions and conditions expressed. The preparation of the various starting materials used in the schemes is well within the skill of persons versed in the art.

Scheme AA

Scheme M is illustrative of a general method for the preparation of compounds of the invention wherein A is amino and R$_3$ is 4,5-dihydro-2-imidazolyl. Instant compounds may be prepared from starting material Compound AA1, purchased from Bachem Bioscience Inc., other compounds such as sulfonyl chloride Compound AA8, purchased from Avocado Research Chemicals Ltd. and amino acid Compound AA3, purchased from Aldrich Chemical Company and reagents such as Compound AA5 purchased from Aldrich Chemical Company.

For the preparation of compounds exemplified by final target Compound 1, the carboxylic acid Compound AA1 was esterified with TMSCHN$_2$ to give the methyl ester Compound AA2. Amino acid Compound AA3 was treated with SOCl$_2$ in benzene, followed by concentration in vacuo of this solution and addition of Compound AA2 dissolved in benzene whereby the quinazoline intermediate Compound AA4 was produced. Allylamine was treated with reagent Compound AA5 to give Compound AA6. The intermediate Compound AA4 was coupled with Compound AA6, followed by removal of the Boc group with TFA to yield a quinazoline intermediate Compound AA7. Intermediate Compound AA7 was then treated with sulfonyl chloride Compound AA8, followed by hydrolysis of the methyl ester thus producing the quinazoline target Compound 1.

SCHEME AA

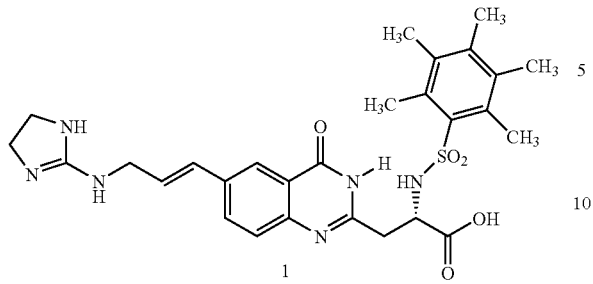

1

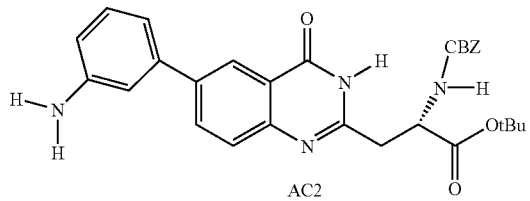

AC2

Scheme AD

Schemes AB–AH describe general synthetic methods whereby other intermediate compounds of the present invention may be prepared using the general procedure of Scheme M and starting materials, compounds and reagents known to those skilled in the art. Additional representative compounds of the present invention can be synthesized using the intermediates prepared in accordance with the Schemes AB–AH described and illustrated below. Since these schemes are illustrations, the invention should not be construed as being limited by the chemical reactions and conditions expressed. The preparation of the various starting materials used in the schemes is well within the skill of persons versed in the art.

The homoallylamine intermediate Compound AD2 was used to replace Compound AA6 to prepare the quinazoline target Compounds 8 and 42. As shown in Scheme AD, a Mitsunobu reaction (O. Mitsunobu, *Synthesis* 1981, 1) of the homoallylalcohol Compound AD1 with di-t-butyl iminodicarboxylate gave the homoallylamine intermediate Compound AD2.

Scheme AB

The allyl-2-aminopyridine intermediate Compound AB2 was used to replace Compound AA6 for the synthesis of the quinazoline target Compound 10 using the procedure of Scheme AA. The intermediate Compound AB2 was produced by treating the substituted or unsubstituted amine Compound AB1 in THF with NaH followed by addition of allylbromide.

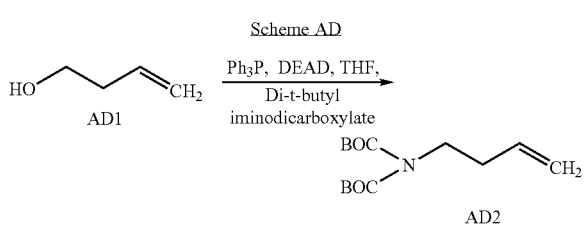

Scheme AE

The allylamine intermediate Compound AE2 was used to replace Compound AA6 to prepare the quinazoline target Compounds 13 and 49. As shown in Scheme AE, the allylisocyanate Compound AE1 was reacted with different primary amines to produce an intermediate Compound AE2.

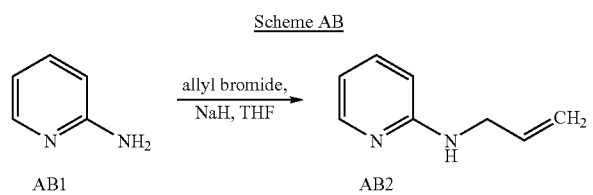

Scheme AC

The quinazoline intermediate Compound AC2 was reacted with Compound AA5 for the synthesis of the quinazoline target Compound 9. As shown in Scheme AC, the quinazoline intermediate Compound AC2 was prepared from the quinazoline intermediate Compound AC1. Compound AC1 was Suzuki cross-coupled with 3-aminophenylboronic acid by a palladium catalyst to produce Compound AC2.

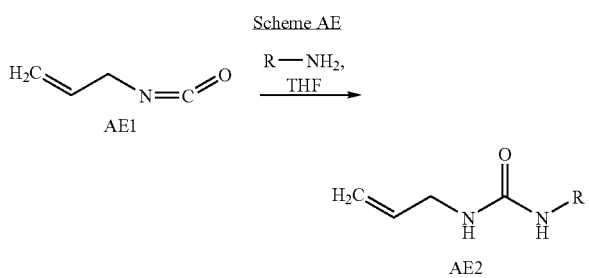

Scheme AF

The allylamine intermediate Compound AF2 was used to replace Compound AA6 to prepare the quinazoline target Compound 15. As shown in scheme AF, Compounds AF1 were treated with trimethyloxonium tetrafluoroborate in dichloromethane and reacted with allylamine to produce intermediate Compounds AF2.

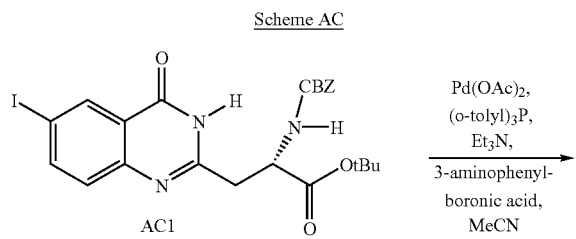

Scheme AF

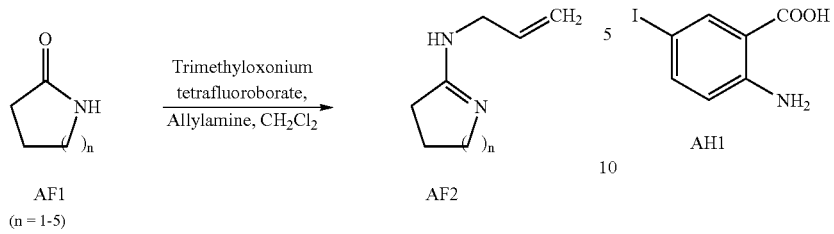

Scheme AG

The allylguanidine intermediate Compounds AG3 and AG4 were used to replace Compound AA6 to prepare the quinazoline target Compound 16. As shown in Scheme AG, a Mitsunobu reaction (O. Mitsunobu, *Synthesis* 1981, 1) of the allyl or homoallylalcohol Compound AG1 with di-t-butyl iminodicarboxylate followed by reduction of the phthalimide gave the allyl or homoallylhydroxyamine intermediate Compound AG2. Intermediate Compound AG2 was reacted with either 1H-pyrazole-1-carboxamidine hydrochloride or 1-methylthio-2-imidazoline hydroiodide to give intermediate Compounds AG3 or AG4, respectively.

Scheme AG

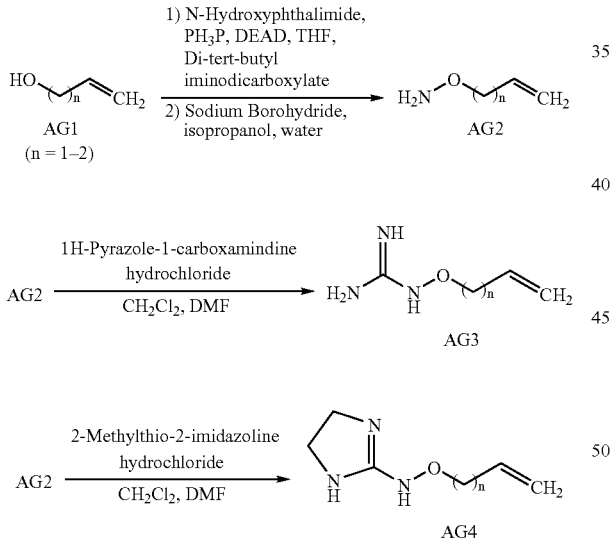

Scheme AH

The iodoquinazolinone intermediate Compounds AH3 and AH4 were used to replace Compound AA4 to prepare the quinazoline target Compounds 17 and 18. As shown in Scheme AH, intermediate Compound AH2 was synthesized with different acetamides. The R group is selected from a substituted or unsubstituted aryl, biaryl or heteroaryl. Intermediate Compound AH2 is then treated with either TBDM-SCI or methyl iodide followed by alkylation with ethyl iodoacetate to give intermediate Compounds AH3 and AH4.

Scheme AH

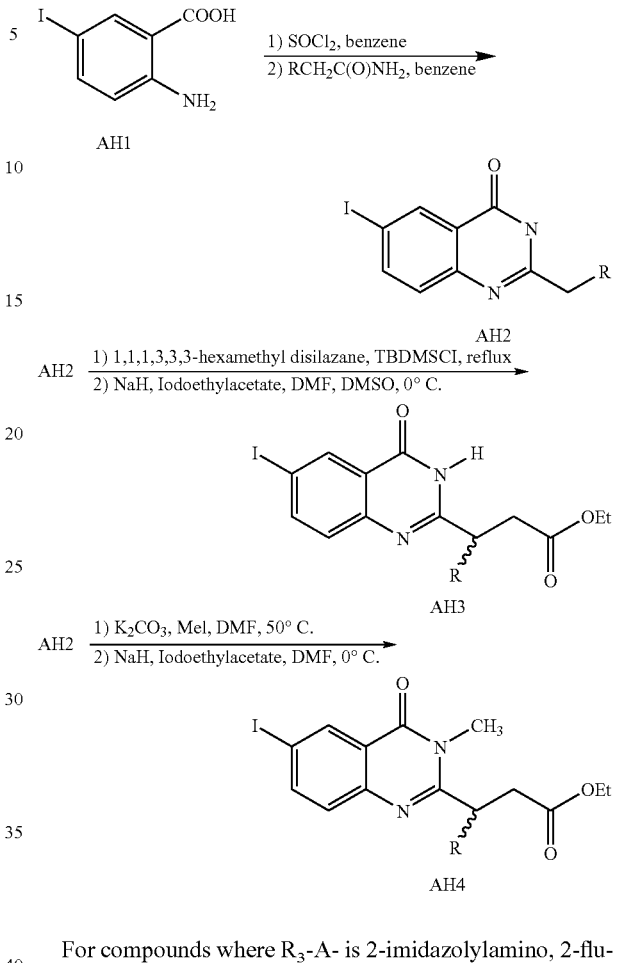

For compounds where $R_3$-A- is 2-imidazolylamino, 2-fluoroimidazole may be reacted with the appropriate alkyl or alkenyl amine as reported (C. Senanayake, *Tetrahedron Lett.* 1999, 40, 6875). For compounds where $R_3$-A- is tetrahydro-2-pyrimidinylamino or 2-pyrimidinylamino, 2-bromopyrimidine may be reacted with the appropriate alkyl or alkenyl amine as reported (G. Hartman, PCT Application WO 95/32710).

Specific Synthetic Methods

Specific compounds which are representative of this invention may be prepared as per the following examples, offered by way of illustration, to aid in the understanding of the invention and should not be construed to limit in any way the invention set forth in the claims which follow thereafter. The instant compounds may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Protected and unprotected amide amino acids and esters were purchased from Bachem Bioscience Inc. Sulfonyl chlorides were purchased from Maybridge Chemical Company, TCI America and Aldrich Chemical Company. All other chemicals were purchased from Aldrich Chemical Company. High field $^1$H NMR spectra were recorded on a Bruker AC-360 spectrometer at 360 MHz, and coupling constants are given in Herz. Melting points were determined on a Mel-Temp II melting point apparatus and are uncorrected. Microanalyses were performed at Robertson Microlit Laboratories, Inc., Madison, N.J. and are expressed in percentage by weight of each element per total molecular weight. In those cases where the product is obtained as a salt, the free base is obtained by methods known to those skilled in the art, e.g. by basic ion exchange purification. Nuclear magnetic resonance (NMR) spectra for hydrogen atoms were measured in the indicated solvent with tetramethylsilane (TMS) as the internal standard on a Bruker AM-360 (360 MHz) spectrometer. The values are expressed in parts per million down field from TMS. The mass spectra (MS) were determined on a Hewlett Packard Series 1050 spectrometer (MH$^+$), using electrospray chemical ionization techniques. Flash column chromatography was conducted with flash column silica gel (40–63 µm). The final products were purified by semipreparative HPLC on a Waters 600E instrument (Waters detector) with a reverse-phase column [Waters Bondapak C18, 40×100 mm (three in series, 125 Å, 15–20 µm), Bondapak C18, 3.9×300 mm (100 Å, 10 µm), or Delta-Pak C18, 8×100 mm (100 Å, 15 µm)], eluting with a mixture of 0.16% TFA in acetonitrile and 0.20% TFA in water in isocratic or gradient modes. Unless otherwise noted, the materials used in the examples were obtained from readily available commercial suppliers or synthesized by standard methods known to anyone skilled in the art of chemical synthesis. The substituent groups, which vary between examples, are hydrogen unless otherwise noted.

Compounds were named according to the nomenclature rules in INDEX NAME PRO Version 4.5, manufactured by Advanced Chemistry Development Inc. of Toronto Canada.

EXAMPLE 1

6-[(1E)-3-[(4,5-dihydro-1H-imidazol-2-yl)amino]-1-propenyl]-(αS)-3,4-dihydro-4-oxo-α-[[(2,3,4,5,6-pentamethylphenyl)sulfonyl]amino]-2-quinazolinepropanoic Acid (1)

A mixture of Compound AA1 (6.45 g, 0.028 mol), DCM (170 mL), and MeOH (30 mL) in a three neck flask fifted with an addition funnel was cooled to 0° C. A 2.0M solution of TMSCHN$_2$ (42 mL, 0.083 mol) in hexanes was added to this mixture via addition funnel over 30 min. The reaction was stirred for 30 minutes at 0° C. The solution was concentrated in vacuo. Diethyl ether (3×100 mL) was added and the solution was concentrated in vacuo to give white solid Compound AA2 (6.8 g, 0.027 mol). Compound AA3 (8.8 g, 0.033 mol), SOCl$_2$ (22 mL, 0.302 mol), and benzene (335 mL) were refluxed for 7 h and cooled to rt. The mixture was concentrated in vacuo to give an oil. Compound AA2 (6.8 g, 0.027 mol) was dissolved in benzene (250 mL) and canulated to the crude oil. The resulting mixture was put aside at room temperature for 3 days. The solid was filtered off and washed with benzene to give Compound AA4 (6.6 g, 0.014 mol). Allylamine (2.6 mL, 0.035 mol), Compound AA5 (9.42 g, 0.039 mol), Et$_3$N (7.3 mL, 0.052 mol), and CHCl$_3$ (175 mL) were refluxed for 20 h. The mixture was concentrated in vacuo and purified by flash silica gel chromatography using DCM/MeOH/NH$_4$OH (90/9/1) to give Compound AA6 (3.5 g. 0.028 mol). Compound AA4 (1.1 g, 0.002 mol), Compound AA6 (1.3 g, 0.010 mol), Pd(OAc)$_2$ (58 mg, 0.26 mmol), tri-o-tolylphosphine (200 mg, 0.66 mmol), Et$_3$N (0.5 mL, 0.003 mol), MeCN (25 mL) was refluxed for 5 h. The mixture was concentrated in vacuo and purified by flash silica gel chromatography using DCM/MeOH/NH$_4$OH (gradient solvent system starting with 500 mL 90/9/1 to 250 mL 50/50 DCM/MeOH to 250 mL MeOH) to give a white solid (0.84 g, 0.002 mol). The white solid was treated with a 50% DCM/TFA (9.0 mL) solution. After 30 min the mixture was concentrated in vacuo. The resulting oil was treated with diethyl ether (3×50 mL) and concentrated in vacuo to give Compound AA7 (1.07 g, 0.002 mol) as the TFA salt. Compound AA7, pentamethylphenylsulfonyl chloride (0.5 g, 0.002 mol), Et$_3$N (0.75 mL, 0.005 mol), and THF (18 mL) were stirred at room temperature for 2 hrs. The mixture was concentrated in vacuo and purified by flash silica gel chromatography using a gradient of 500 mL DCM/MeOH/NH$_4$OH (90/9/1) to 250 mL DCM/MeOH (50/50) to 250 mL MeOH to give a white solid (0.52 g, 0.001 mol). The white solid (120 mg, 0.21 mol) was dissolved in THF (1 mL) and cooled to 0° C. Lithium hydroxide (25 mg, 0.6 mol) was dissolved in water and added to the cooled solution. The mixture was stirred at room temperature for 4 h. The reaction was neutralized with TFA and concentrated in vacuo. The crude mixture was purified by reverse-phase semipreparative HPLC using a gradient of water/acetonitrile 90/10 to 70/30 over 1 hr to 10/90 over 30 min to give Compound 1 as a white solid (TFA salt): m.p. 131–135° C.; $^1$H NMR (CD$_3$OD) δ 1.8 (s, 9 H), 2.4 (s, 6 H), 2.8 (m, 1 H), 3.3 (m, 1 H), 3.7 (s, 4 H), 4.1 (d, J=5 Hz, 2 H), 4.6 (m, 1 H), 6.4 (dt, J=16 Hz, 6 Hz, 1 H), 6.7 (d, J=16 Hz, 1 H), 7.4 (d, J=8 Hz, 1 H), 7.8 (d, J=8 Hz, 1 H), 7.9 (s, 1 H); MS m/e 567 (MH$^+$); Anal. calcd. for C$_{28}$H$_{34}$N$_6$O$_5$S$_1$.2.1 CF$_3$CO$_2$H.1.0H$_2$O (566.23/824.15): C, 46.93; H, 4.66; N, 10.20; F, 14.52; H$_2$O 2.19. Found: C, 46.95; H, 4.79; N, 10.09; F, 14.77; H$_2$O, 2.05.

As described in the following examples, other compounds of the present invention may be prepared using the procedure of Example 1 and the appropriate starting materials, compounds and reagents known to those skilled in the art.

EXAMPLE 2

6-[(1E)-3-[(4,5-dihydro-1H-imidazol-2-yl)amino]-1-propenyl]-(αS)-3,4-dihydro-4-oxo-α-[[(phenylmethoxy)carbonyl]amino]-2-quinazolinepropanoic Acid (2)

Compound 2 was prepared as described for Compound 1, but N-carbobenzyloxyasparagine tert-butyl ester (8.2 g) was employed instead of Compound AA2; Compound 2 was isolated as a white solid (TFA salt): $^1$H NMR (DMSO, d$_6$) δ 3.0 (m, 1 H), 3.2 (m, 1 H), 3.7 (s, 4 H), 4.0 (m, 2 H), 4.7 (m, 1 H), 5.0 (s, 2 H), 6.4 (dt, J=16 Hz, 6 Hz, 1 H), 6.7 (d, J=16 Hz, 1 H), 7.3 (m, 5 H), 7.6 (d, J=8 Hz, 1 H), 7.8 (d, J=8 Hz, 1 H), 8.1 (s, 1 H); MS m/e 491 (MH$^+$).

EXAMPLE 3

6-[(1E)-3-[(4,5-dihydro-1H-imidazol-2-yl)amino]-1-propenyl]-(αS)-3,4-dihydro-4-oxo-a-[[(2,4,6-trimethylphenyl)sulfonyl]amino]-2-quinazolinepropanoic Acid (3)

Compound 3 was prepared as described for Compound 1 from Compound AA7 (0.5 g) and 2,4,6-trimethylbenzenesulfonyl chloride (0.33 g). Compound 3 was isolated as a white solid (TFA salt): $^1$H NMR (CD$_3$OD) δ 2.1 (s, 3 H), 2.2 (s, 6 H), 2.8 (m, 1 H), 3.3 (m, 1 H), 3.7 (s, 4 H), 4.1 (d, J=5

Hz, 2 H), 4.6 (m, 1 H), 6.5 (dt, J=16 Hz, 6 Hz, 1 H), 6.8 (d, J=16 Hz, 1 H), 7.3 (s, 2 H), 7.4 (d, J=8 Hz, 1 H), 7.8 (d, J=8 Hz, 1 H), 8.0 (s, 1 H); MS m/e 539 (MH$^+$).

EXAMPLE 4

6-[(1E)-3-[(4,5-dihydro-1H-imidazol-2-yl)amino]-1-propenyl]-($\alpha$S)-3,4-dihydro-4-oxo-$\alpha$-[(8-quinolinylsulfonyl)amino]-2-quinazolinepropanoic Acid (4)

Compound 4 was prepared as described for Compound 1 from Compound AA7 (0.5 g) and 8-quinolinesulfonyl chloride (0.34 g). Compound 4 was isolated as a white solid (TFA salt): $^1$H NMR (CD$_3$OD) $\delta$ 3.1 (m, 2 H), 3.7 (s, 4 H), 4.1 (d, J=5 Hz, 2 H), 4.8 (m, 1 H), 6.4 (dt, J=16 Hz, 6 Hz, 1 H), 6.7 (d, J=16 Hz, 1 H), 7.3 (m, 2 H), 7.6 (m, 1 H), 7.9 (d, J=8 Hz, 1 H), 8.0 (m, 2 H), 8.2 (d, J=8 Hz, 1 H), 8.3 (D, J=8 Hz, 1 H), 8.7 (s, 1 H); MS m/e 548 (MH$^+$).

EXAMPLE 5

6-[(1E)-3-[(4,5-dihydro-1H-imidazol-2-yl)amino]-1-propenyl]-($\alpha$S)-3,4-dihydro-$\alpha$-[[[2-(1-naphthalenyl)ethyl]sulfonyl]amino]-4-oxo-2-quinazolinepropanoic Acid (5)

Compound 5 was prepared as described for Compound 1 from Compound AA7 (0.16 g) and 2-(1-naphthyl)ethanesulfonyl chloride (0.13 g). Compound 5 was isolated as a white solid (TFA salt): $^1$H NMR (CD$_3$OD) $\delta$ 3.1 (m, 2 H), 3.3 (m, 2 H), 3.5 (m, 2 H), 3.7 (s, 4 H), 4.1 (d, J=5 Hz, 2 H), 4.8 (m, 1 H), 6.4 (dt, J=16 Hz, 6 Hz, 1 H), 6.7 (d, J=16 Hz, 1 H), 7.2 (m, 1 H), 7.3 (m, 2 H), 7.5 (m, 3 H), 7.7 (m, 2 H), 7.8 (m, 2 H), 8.1 (s, 1 H); MS m/e 575 (MH$^+$).

EXAMPLE 6

6-[(1E)-3-[(4,5-dihydro-1H-imidazol-2-yl)amino]-1-propenyl]-($\alpha$S)-3,4-dihydro-4-oxo-$\alpha$-[[[5-(2-pyridinyl)-2-thienyl]sulfonyl]amino]-2-quinazolinepropanoic Acid (6)

Compound 6 was prepared as described for Compound 1 from Compound AA7 (0.1 g) and 5-(pyrid-2-yl)thiophene-2-sulfonyl chloride (0.06 g). Compound 6 was isolated as a white solid (TFA salt): $^1$H NMR (CD$_3$OD) $\delta$ 2.9 (m, 1 H), 3.1 (m, 1 H), 3.7 (s, 4 H), 4.0 (d, J=5 Hz, 2 H), 4.5 (m, 1 H), 6.1 (dt, J=16 Hz, 6 Hz, 1 H), 6.4 (d, J=16 Hz, 1 H), 7.2 (m, 2 H), 7.3 (m, 3 H), 7.6 (m, 1 H), 7.7 (m, 1 H), 7.8 (m, 1 H), 8.3 (s, 1 H); MS m/e 580 (MH$^+$).

EXAMPLE 7

6-[(1E)-3-[(4,5-dihydro-1H-imidazol-2-yl)amino]-1-propenyl]-($\alpha$S)-3,4-dihydro-4-oxo-$\alpha$-[[[(E)-2-phenylethenyl]sulfonyl]amino]-2-quinazolinepropanoic Acid (7)

Compound 7 was prepared as described for Compound 1 from Compound AA7 (0.1 g) and trans-p-styrenesulfonyl chloride (0.06 g). Compound 7 was isolated as a white solid (TFA salt): $^1$H NMR (CD$_3$OD) $\delta$ 3.1 (m, 1 H), 3.3 (m, 1 H), 3.7 (s, 4 H), 4.1 (d, J=5 Hz, 2 H), 4.6 (m, 1 H), 6.4 (dt, J=16 Hz, 6 Hz, 1 H), 6.7 (d, J=16 Hz, 1 H), 6.9 (d, J=16 Hz, 1 H), 7.3 (m, 6 H), 7.6 (d, J=8 Hz, 1 H), 7.9 (d, J=8 Hz, 1 H), 8.1 (s, 1 H); MS m/e 521 (MH$^+$).

EXAMPLE 8

6-[(1E)-4-[(4,5-dihydro-1H-imidazol-2-yl)amino]-1-butenyl]-($\alpha$S)-3,4-dihydro-4-oxo-$\alpha$-[[(phenylmethoxy)carbonyl]amino]-2-quinazolinepropanoic Acid (8)

Compound 8 was prepared as described for Compound 1, but N-carbobenzyloxyasparagine tert-butyl ester (8.2 g) was employed instead of Compound AA2. Intermediate Compound AD2 (4.9 g, Scheme AD) was used instead of Compound AA6. The 4,5-dihydro-1H-imidazol-2-yl derivative was synthesized utilizing AA5 with the corresponding butenylamine version of AA7.

Compound 8 was isolated as a white solid (TFA salt): $^1$H NMR (DMSO, d$_6$) $\delta$ 3.0 (m, 1 H), 3.2 (m, 1 H), 3.4 (m, 2 H), 3.6 (m, 2 H), 3.7 (s, 4 H), 4.7 (m, 1 H), 5.0 (s, 2 H), 6.4 (dt, J=16 Hz, 6 Hz, 1 H), 6.7 (d, J=16 Hz, 1 H), 7.3 (m, 5 H), 7.6 (d, J=8 Hz, 1 H), 7.8 (d, J=8 Hz, 1 H), 8.1 (s, 1 H); MS m/e 505 (MH$^+$).

EXAMPLE 9

6-[3-[(4,5-dihydro-1H-imidazol-2-yl)amino]phenyl]-($\alpha$S)-3,4-dihydro-4-oxo-$\alpha$-[[(phenylmethoxy)carbonyl]amino]-2-quinazolinepropanoic Acid (9)

Compound 9 was prepared as described for Compound 1, but instead of Compound AA2, N-carbobenzyloxyasparagine tert-butyl ester (8.2 g) was reacted with Compound AA3 and produced Compound AC1. Scheme AC shows the Suzuki cross coupling of Compound AC1 with 3-aminophenylboronic acid to produce Compound AC2. As shown in the illustration for Scheme AA, intermediate Compound AC2 (0.19 g) was converted to the corresponding 2-aminoimidazoline by coupling with Compound AA5 followed by hydrolysis to yield Compound 9. Compound 9 was isolated as a white solid (TFA salt): $^1$H NMR (DMSO, d$_6$) $\delta$ 3.0 (m, 1 H), 3.2 (m, 1 H), 3.4 (m, 2 H), 3.6 (s, 4H), 4.7 (m, 1 H), 5.0 (s, 2 H), 7.0 (m, 1 H), 7.3 (m, 5 H), 7.5 (m, 2 H), 7.7 (d, J=8 Hz, 1 H), 7.8 (d, J=8 Hz, 1 H), 8.1 (d, J=8 Hz, 1 H), 8.3 (s, 1 H); MS m/e 527 (MH$^+$).

EXAMPLE 10

($\alpha$S)-3,4-dihydro-4-oxo-$\alpha$-[[(2,3,4,5,6-pentamethylphenyl)sulfonyl]amino]-6-[(1E)-3-(2-pyridinylamino)-1-propenyl]-2-quinazolinepropanoic Acid (10)

Compound 10 was prepared as described for Compound 1, but Compound AB2 (0.6 g) was used instead of Compound AA6. Compound 10 was isolated as a white solid (TFA salt): m.p. 148–151° C.; $^1$H NMR (CD$_3$OD) $\delta$ 1.9 (s, 9 H), 2.4 (s, 6 H), 2.9 (m, 1 H), 3.3 (m, 1 H), 4.4 (d, J=5 Hz, 2 H), 4.7 (m, 1 H), 6.6 (dt, J=16 Hz, 6 Hz, 1 H), 6.9 (d, J=16 Hz, 1 H), 7.0 (t, J=7 Hz, 1 H), 7.2 (d, J=8 Hz, 1 H), 7.4 (d, J=8 Hz, 1 H), 8.0 (m, 4 H); MS m/e 576 (MH$^+$); Anal. Calcd. for C$_{30}$H$_{33}$N$_5$O$_5$S$_1$.2.4 CF$_3$CO$_2$H.1.0H$_2$O (575.22/867.36): C, 48.19; H, 4.35; N, 8.07; F, 15.77; H$_2$O 2.08. Found: C, 47.93; H, 4.31; N, 7.92; F, 15.85; H$_2$O, 2.21.

EXAMPLE 11

(αS)-3,4-dihydro-4-oxo-α-[[(2,3,4,5,6-pentamethylphenyl)sulfonyl]amino]-6-[3-(2-pyridinylamino)propyl]-2-quinazolinepropanoic Acid (11)

Compound 11 was prepared as described for Compound 1, but after Compounds AA4 and AB2 were coupled the double bond was hydrogenated using 10% Pd/C (0.08 g) in MeOH (20 mL) at 50 psi hydrogen for 2 hrs. Compound 11 was isolated as a white solid (HCl salt): m.p. 218–221° C.; $^1$H NMR (CD$_3$OD) δ 1.9 (s, 9 H), 2.0 (m, 2 H), 2.5 (s, 6 H), 2.8 (m, 1 H), 3.2 (m, 1 H), 3.5 (m, 2 H), 4.5 (m, 1 H), 6.9 (t, J=6 Hz, 1 H), 7.1 (d, J=8 Hz, 1 H), 7.2 (d, J=8 Hz, 1 H), 7.6 (d, J=8 Hz, 1 H), 7.8 (s, 1 H), 7.9 (m, 4 H), 8.1 (d, J=8 Hz, 1 H); MS m/e 578 (MH$^+$); Anal. Calcd. for C$_{30}$H$_{35}$N$_5$O$_5$S$_1$.2.0 HCl.0.8 H$_2$O (577.24/665.04): C, 54.18; H, 5.85; N, 10.53; Cl, 10.66; H$_2$O 2.17. Found: C, 54.21; H, 5.79; N, 10.44; Cl, 10.49; H$_2$O, 2.12.

EXAMPLE 12

(αS)-3,4-dihydro-4-oxo-α-[[(phenylamino)carbonyl]amino]-6-[(E)-3-(2-pyridinylamino)-1-propenyl]-2-quinazolinepropanoic Acid (12)

Compound 12 was prepared as described for Compound 1, but phenylisocyanate (0.03 mL) was used in place of sulfonyl chloride Compound AA8. Compound 12 was isolated as a white solid (TFA salt); $^1$H NMR (CD$_3$OD) δ 3.3 (m, 1 H), 3.5 (m, 1 H), 4.3 (d, J=6 Hz, 2 H), 5.0 (m, 1 H), 6.6 (dt, J=16 Hz, 6 Hz, 1 H), 6.8 (d, J=16 Hz, 1 H), 7.0 (m, 2 H), 7.2 (m, 5 H), 7.7 (d, J=8 Hz, 1H), 7.9 (d, J=8 Hz, 1 H), 8.0 (m, 2 H), 8.3 (s, 1 H); MS m/e 485 (MH$^+$).

EXAMPLE 13

(αS)-3,4-dihydro-4-oxo-α-[[(2,3,4,5,6-pentamethylphenyl)sulfonyl]amino]-6-[(1E)-3-[[(phenylamino)carbonyl]amino]-1-propenyl]-2-quinazolinepropanoic Acid (13)

Compound 13 was prepared as described for Compound 1, but Compound AE2 (R=Phenyl) (0.9 g) was used in place of Compound AA6. Compound 13 was isolated as a white solid (TFA salt); $^1$H NMR (CD$_3$OD) δ 1.8 (s, 9 H), 2.3 (s, 6 H), 2.9 (m, 1 H), 3.2 (m, 1 H), 4.0 (m, 2 H), 4.6 (m, 1 H), 6.4 (m, 1 H), 6.7 (d, J=16 Hz, 1 H), 6.9 (m, 1 H), 7.2 (m, 1 H), 7.4 (m, 1 H), 7.8 (m, 1 H), 8.1 (m, 2 H), 8.6 (s, 1 H); MS m/e 618 (MH$^+$).

EXAMPLE 14

(βR)-3,4-dihydro-4-oxo-β-[[(2,3,4,5,6-pentamethylphenyl)sulfonyl]amino]-6-[(1E)-3-(2-pyridinylamino)-1-propenyl]-2-quinazolinepropanoic Acid (14)

Compound 14 was prepared as described for Compound 1, but Boc-D-isoasparagine (4.0 g) was used instead of Compound AA1. Compound 14 was isolated as a white solid (TFA salt); $^1$H NMR (CD$_3$OD) δ 1.8 (s, 9 H), 2.5 (s, 6 H), 2.9 (m, 1 H), 3.1 (m, 1 H), 4.3 (d, J=5 Hz, 2 H), 4.6 (m, 1 H), 6.5 (dt, J=16 Hz, 6 Hz, 1 H), 6.8 (d, J=16 Hz, 1 H), 7.0 (t, J=6 Hz, 1 H), 7.1 (d, J=9 Hz, 1 H), 7.5 (d, J=8 Hz, 1 H), 7.9 (m, 4 H); MS m/e 576 (MH$^+$).

EXAMPLE 15

6-[(1E)-3-[(3,4-dihydro-2H-pyrrol-5-yl)amino]-1-propenyl]-(αS)-3,4-dihydro-4-oxo-α-[[(2,3,4,5,6-pentamethylphenyl)sulfonyl]amino]-2-quinazolinepropanoic Acid (15)

Compound 15 was prepared as described for Compound 1, but AF2 (n=1) (0.458 g) was used in place of Compound AA6. Compound 15 was isolated as a white solid (TFA salt); $^1$H NMR (CD$_3$OD) δ 1.8 (s, 9 H), 2.2 (m, 2H), 2.4 (s, 6 H), 2.9 (m, 2 H), 3.2 (m, 2 H), 3.7 (m, 2H), 4.0 (m, 2 H), 4.6 (m, 1 H), 6.4 (m, 1 H), 6.8 (d, J=16 Hz, 1 H), 7.3 (m, 1 H), 7.8 (m, 2 H), 7.9 (s, 1 H); MS m/e 566 (MH$^+$).

EXAMPLE 16

6-[(1E)-4-[[(aminoiminomethyl)amino]oxy]-1-butenyl]-(αS)-3,4-dihydro-4-oxo-α-[[(2,3,4,5,6-pentamethylphenyl)sulfonyl]amino]-2-quinazolinepropanoic Acid (16)

Compound 16 was prepared as described for Compound 1, but AG3 (n=2) (0.219 g) was used in place of Compound AA6. Compound 16 was isolated as a white solid (TFA salt); $^1$H NMR (CD$_3$OD) δ 1.8 (s, 9H), 2.4 (s, 6 H), 2.8 (m, 3 H), 3.2 (m, 21H), 4.0 (m, 2 H), 4.6 (m, 1 H), 6.4 (m, 1 H), 6.8 (m, 1 H), 7.3 (m, 1 H), 7.8 (m, 2 H), 7.9 (s, 1 H); MS m/e 571 (MH$^+$).

EXAMPLE 17

(βR)-3,4-dihydro-β-(3-methoxyphenyl)-4-oxo-6-[(1E)-3-(2-pyridinylamino)-1-propenyl]-2-quinazolinepropanoic Acid (17)

Compound 17 was prepared as described for Compound 1, but Compound AH3 (R=3-Methoxyphenyl) (0.49 g) was used instead of Compound AA4. Compound 17 was isolated as a white solid (TFA salt); $^1$H NMR (CD$_3$OD) δ 2.9 (m, 1 H), 3.3 (m, 2 H), 3.7 (s, 3 H), 4.2 (m, 2 H), 6.6 (m, 1 H), 6.9 (m, 5 H), 7.1 (m, 1 H), 7.2 (m, 1 H), 7.6 (s, 1 H), 7.9 (m, 3 H), 8.2 (s, 1 H); MS m/e 457 (MH$^+$).

EXAMPLE 18

(βR)-3,4-dihydro-β-(3-methoxyphenyl)-3-methyl-4-oxo-6-[(1E)-3-(2-pyridinylamino)-1-propenyl]-2-quinazolinepropanoic Acid (18)

Compound 18 was prepared as described for Compound 1, but Compound AH4 (R=3-Methoxyphenyl) (4.0 g) was used instead of Compound AA4. Compound 18 was isolated as a white solid (TFA salt); $^1$H NMR (CD$_3$OD) δ 2.8 (m, 2 H), 3.5 (m, 4 H), 3.7 (s, 3H), 4.2 (d, 2 H), 6.5 (m, 1 H), 6.9 (m, 4 H), 7.1 (d, 1H), 7.2 (t, 1 H), 7.7 (d, 1 H), 7.9 (m, 3 H), 8.1 (s, 1 H); MS m/e 471 (MH$^+$).

EXAMPLES 19–82

Following the procedure of Example 1 and substituting the appropriate starting materials, compounds and reagents, the following Compounds 19–82 of the invention were also prepared:

| Cpd | Name | MS m/e (MH+). |
|---|---|---|
| (19) | 6-[(1E)-3-amino-1-propenyl]-(αS)-3,4-dihydro-4-oxo-α-[[(phenylmethoxy)carbonyl]amino]-2-quinazolinepropanoic acid | 423 |
| (20) | 6-[3-[(4,5-dihydro-1H-imidazol-2-yl)amino]-1-propynyl]-(αS)-3,4-dihydro-4-oxo-α-[[(phenylmethoxy)carbonyl] amino]-2-quinazolinepropanoic acid | 489 |
| (21) | 6-[(1E)-3-[(4,5-dihydro-1H-imidazol-2-yl)amino]-1-propenyl]-(αS)-3,4-dihydro-4-oxo-α-[[(2,4,6-trichlorophenyl)sulfonyl]amino]-2-quinazolinepropanoic acid | 601 |
| (22) | 6-[(1E)-3-[(4,5-dihydro-1H-imidazol-2-yl)amino]-1-propenyl]-α-[[[5-(dimethylamino)-1-naphthalenyl]sulfonyl]amino]-(αS)-3,4-dihydro-4-oxo-2-quinazolinepropanoic acid | 590 |
| (23) | α-[[[4-(1,1-dimethylethyl)phenyl]sulfonyl]amino]-(αS)-3,4-dihydro-4-oxo-6-[(1E)-3-(2-pyridinylamino)-1-propenyl]-2-quinazolinepropanoic acid | 562 |
| (24) | (αS)-3,4-dihydro-α-[(2-naphthalenylsulfonyl)amino]-4-oxo-6-[(1E)-3-(2-pyridinylamino)-1-propenyl]-2-quinazolinepropanoic acid | 556 |
| (25) | (αS)-3,4-dihydro-4-oxo-6-[(1E)-3-(2-pyridinylamino)-1-propenyl]-α-[[[4-(trifluoromethyl)phenyl]sulfonyl]amino]-2-quinazolinepropanoic acid | 574 |
| (26) | (αS)-3,4-dihydro-α-[[(4-methoxyphenyl)sulfonyl]amino]-4-oxo-6-[(1E)-3-(2-pyridinylamino)-1-propenyl]-2-quinazolinepropanoic acid | 536 |
| (27) | (αS)-3,4-dihydro-6-[(1E)-3-(2-imino-1-pyrrolidinyl)-1-propenyl]-4-oxo-α-[[(2,3,4,5,6-pentamethylphenyl)sulfonyl]amino]-2-quinazolinepropanoic acid | 566 |
| (28) | (αS)-3,4-dihydro-4-oxo-α-[[[5-(phenylsulfonyl)-2-thienyl]sulfonyl]amino]-6-[(1E)-3-(2-pyridinylamino)-1-propenyl]-2-quinazolinepropanoic acid | 652 |
| (29) | α-[[(2-chloro-6-methylphenyl)sulfonyl]amino]-(αS)-3,4-dihydro-4-oxo-6-[(1E)-3-(2-pyridinylamino)-1-propenyl]-2-quinazolinepropanoic acid | 555 |
| (30) | (αS)-3,4-dihydro-6-[(1E)-3-[(1-methyl-1H-imidazol-2-yl)amino]-1-propenyl]-4-oxo-α-[[(2,3,4,5,6-pentamethylphenyl)sulfonyl]amino]-2-quinazolinepropanoic acid | 579 |
| (31) | (αS)-3,4-dihydro-α-[[[5-(3-isoxazolyl)-2-thienyl]sulfonyl]amino]-4-oxo-6-[(1E)-3-(2-pyridinylamino)-1-propenyl]-2-quinazolinepropanoic acid | 579 |
| (32) | α-[[(2,5-dimethoxyphenyl)sulfonyl]amino]-(αS)-3,4-dihydro-4-oxo-6-[(1E)-3-(2-pyridinylamino)-1-propenyl]-2-quinazolinepropanoic acid | 566 |
| (33) | α-[[(3,4-dimethoxyphenyl)sulfonyl]amino]-(αS)-3,4-dihydro-4-oxo-6-[(1E)-3-(2-pyridinylamino)-1-propenyl]-2-quinazolinepropanoic acid | 566 |
| (34) | (αS)-3,4-dihydro-4-oxo-6-[(1E)-3-(2-pyridinylamino)-1-propenyl]-α-[2-thienylsulfonyl)amino]-2-quinazolinepropanoic acid | 512 |
| (35) | (αS)-3,4-dihydro-4-oxo-6-[(1E)-3-(2-pyridinylamino)-1-propenyl]-α-[[[4-(trifluoromethoxy)phenyl]sulfonyl]amino]-2-quinazolinepropanoic acid | 590 |
| (36) | α-[[(5-chloro-1,3-dimethyl-1H-pyrazol-4-yl)sulfonyl]amino]-(αS)-3,4-dihydro-4-oxo-6-[(1E)-3-(2-pyridinylamino)-1-propenyl]-2-quinazolinepropanoic acid | 559 |
| (37) | α-[[(3,5-dimethyl-4-isoxazolyl)sulfonyl]amino]-(αS)-3,4-dihydro-4-oxo-6-[(1E)-3-(2-pyridinylamino)-1-propenyl]-2-quinazolinepropanoic acid | 525 |
| (38) | (αS)-3,4-dihydro-6-[(1E)-3-[(3-methyl-2-pyridinyl)amino]-1-propenyl]-4-oxo-α-[[(2,3,4,5,6-pentamethylphenyl)sulfonyl]amino]-2-quinazolinepropanoic acid | 590 |
| (39) | 6-[(1E)-3-[(5-chloro-2-pyridinyl)amino]-1-propenyl]-(αS)-3,4-dihydro-4-oxo-α-[[(2,3,4,5,6-pentamethylphenyl)sulfonyl]amino]-2-quinazolinepropanoic acid | 611 |
| (40) | 6-[(1E)-3-[(5-chloro-2-pyridinyl)amino]-1-propenyl]-(αS)-3,4-dihydro-α-[[(4-methoxyphenyl)sulfonyl]amino]-4-oxo-2-quinazolinepropanoic acid | 571 |
| (41) | 6-[(1E)-3-[(4,5-dihydro-1H-imidazol-2-yl)amino]-1-propenyl]-(αS)-3,4-dihydro-4-oxo-α-[[(2,3,4,5,6-pentamethylphenyl)sulfonyl]amino]methyl ester 2-quinazolinepropanoic acid | 581 |
| (42) | 6-[(1E)-4-[(4,5-dihydro-1H-imidazol-2-yl)amino]-1-butenyl]-(αS)-3,4-dihydro-4-oxo-α-[[(2,3,4,5,6-pentamethylphenyl)sulfonyl]amino]-2-quinazolinepropanoic acid | 581 |
| (43) | (αS)-3,4-dihydro-6-[(1E)-3-[(5-methyl-2-pyridinyl)amino]-1-propenyl]-4-oxo-α-[[(2,3,4,5,6-pentamethylphenyl)sulfonyl]amino]-2-quinazolinepropanoic acid | 590 |

-continued

| Cpd | Name | MS m/e (MH+). |
|---|---|---|
| (44) | α-[[(3,4-dimethoxyphenyl)sulfonyl]amino]-(αS)-3,4-dihydro-6-[(1E)-3-[(5-methyl-2-pyridinyl)amino]-1-propenyl]-4-oxo-2-quinazolinepropanoic acid | 580 |
| (45) | (αS)-3,4-dihydro-6-[(1E)-3-[(4-methyl-2-pyridinyl)amino]-1-propenyl]-4-oxo-α-[[(2,3,4,5,6-pentamethylphenyl)sulfonyl]amino]-2-quinazolinepropanoic acid | 590 |
| (46) | α-[[(3,4-dimethoxyphenyl)sulfonyl]amino]-(αS)-3,4-dihydro-6-[(1E)-3-[(4-methyl-2-pyridinyl)amino]-1-propenyl]-4-oxo-2-quinazolinepropanoic acid | 580 |
| (47) | (αS)-3,4-dihydro-6-[(1E)-3-[(imino-3-pyridinylmethyl)amino]-1-propenyl]-4-oxo-α-[[(2,3,4,5,6-pentamethylphenyl)sulfonyl]amino]-2-quinazolinepropanoic acid | 603 |
| (48) | 6-[(1E)-3-[(4,5-dihydro-1H-imidazol-2-yl)amino]-1-propenyl]-α-[[(3,4-dimethoxyphenyl)sulfonyl]amino]-(αS)-3,4-dihydro-4-oxo-2-quinazolinepropanoic acid | 557 |
| (49) | (αS)-3,4-dihydro-4-oxo-α-[[(2,3,4,5,6-pentamethylphenyl)sulfonyl]amino]-6-[(1E)-3-[[(benzylamino)carbonyl]amino]-1-propenyl]-2-quinazolinepropanoic acid | 632 |
| (50) | 6-[(1E)-3-[(4,5-dihydro-1H-imidazol-2-yl)amino]-1-propenyl]-(αS)-3,4-dihydro-α-[[(4-methoxyphenyl)sulfonyl]amino]-4-oxo-2-quinazolinepropanoic acid | 527 |
| (51) | 6-[(1E)-3-[[(butylamino) carbonyl]amino]-1-propenyl]-(αS)-3,4-dihydro-4-oxo-α-[[(2,3,4,5,6-pentamethylphenyl)sulfonyl]amino]-2-quinazolinepropanoic acid | 598 |
| (52) | (αS)-3,4-dihydro-4-oxo-α-($α^2$S)-[[(2,3,4,5,6-pentamethylphenyl)sulfonyl]amino]-6-[(1E)-3-[(3,4,5,6-tetrahydro-2-pyridinyl)amino]-1-propenyl]-2-quinazolinepropanoic acid | 580 |
| (53) | 6-[(1E)-3-[(aminocarbonyl)amino]-1-propenyl]-(αS)-3,4-dihydro-4-oxo-α-[[(2,3,4,5,6-pentamethylphenyl)sulfonyl]amino]-2-quinazolinepropanoic acid | 542 |
| (54) | α-[[(3,4-dimethoxyphenyl)sulfonyl]amino]-(αS)-3,4-dihydro-4-oxo-6-[(1E)-3-[[[(phenylmethyl)amino]carbonyl]amino]-1-propenyl]-2-quinazolinepropanoic acid | 622 |
| (55) | 6-[(1E)-3-[(3,4-dihydro-2H-pyrrol-5-yl)amino]-1-propenyl]-α-[[(3,4-dimethoxyphenyl)sulfonyl]amino]-(αS)-3,4-dihydro-4-oxo-2-quinazolinepropanoic acid | 556 |
| (56) | (αS)-3,4-dihydro-α-[[(4-methoxy-2,3,6-trimethylphenyl)sulfonyl]amino]-4-oxo-6-[(1E)-3-[[[(phenylmethyl)amino]carbonyl]amino]-1-propenyl]-2-quinazolinepropanoic acid | 634 |
| (57) | (αS)-3,4-dihydro-α-[[(4-methoxyphenyl)sulfonyl]amino]-4-oxo-6-[(1E)-3-[[[(phenylmethyl)amino]carbonyl]amino]-1-propenyl]-2-quinazolinepropanoic acid | 592 |
| (58) | (αS)-3,4-dihydro-6-[(1E)-3-[[[(1-methylethyl)amino]carbonyl]amino]-1-propenyl]-4-oxo-α-[[(2,3,4,5,6-pentamethylphenyl)sulfonyl]amino]-2-quinazolinepropanoic acid | 584 |
| (59) | (αS)-3,4-dihydro-6-[(1E)-3-[[(methylamino)carbonyl]amino]-1-propenyl]-4-oxo-α-[[(2,3,4,5,6-pentamethylphenyl)sulfonyl]amino]-2-quinazolinepropanoic acid | 556 |
| (60) | α-[[(3,4-dimethoxyphenyl)sulfonyl]amino]-(αS)-3,4-dihydro-4-oxo-6-[(1E)-3-[(3,4,5,6-tetrahydro-2-pyridinyl)amino]-1-propenyl]-2-quinazolinepropanoic acid | 570 |
| (61) | 6-[(1E)-3-[(3,4-dihydro-4-oxo-2-quinazolinyl)amino]-1-propenyl]-(αS)-3,4-dihydro-4-oxo-α-[[(2,3,4,5,6-pentamethylphenyl)sulfonyl]amino]-2-quinazolinepropanoic acid | 643 |
| (62) | (αS)-3,4-dihydro-4-oxo-6-[(1E)-3-[[[(phenylmethyl)amino]carbonyl]amino]-1-propenyl]-α-[[(2,4,6-trimethylphenyl)sulfonyl]amino]-2-quinazolinepropanoic acid | 604 |
| (63) | 6-[(1E)-3-[(4,5-dihydro-1H-imidazol-2-yl)amino]-1-propenyl]-(αS)-3,4-dihydro-α-[[(4-methoxyphenoxy)carbonyl]amino]-4-oxo-2-quinazolinepropanoic acid | 507 |
| (64) | (αS)-3,4-dihydro-6-[1-[[[[(1-methylethyl)amino]carbonyl]amino]methyl]ethenyl]-4-oxo-α-[[(2,3,4,5,6-pentamethylphenyl)sulfonyl]amino]-2-quinazolinepropanoic acid | 584 |
| (65) | α-[[(5-chloro-1,3-dimethyl-1H-pyrazol-4-yl)sulfonyl]amino]-(αS)-3,4-dihydro-4-oxo-6-[(1E)-3-[[[(phenylmethyl)amino]carbonyl]amino]-1-propenyl]-2-quinazolinepropanoic acid | 615 |
| (66) | (αS)-3,4-dihydro-4-oxo-α-[[(2,3,4,5,6-pentamethylphenyl)sulfonyl]amino]-6-[(1E)-3-[[[[(2S)-2-phenylcyclopropyl]amino]carbonyl]amino]-1-propenyl]-2-quinazolinepropanoic acid | 658 |
| (67) | 6-[(1E)-3-[(3,4-dihydro-2H-pyrrol-5-yl)amino]-1-propenyl]-(αS)-3,4-dihydro-4-oxo-α-[[(phenylmethoxy)carbonyl]amino]-2-quinazolinepropanoic acid | 490 |

-continued

| Cpd | Name | MS m/e (MH+). |
|---|---|---|
| (68) | α-[[(3,4-dimethoxyphenyl)sulfonyl]amino]-6-[(1E)-3-[(3,4,5,6,7,8-hexahydro-2-azocinyl)amino]-1-propenyl]-(αS)-3,4-dihydro-4-oxo-2-quinazolinepropanoic acid | 598 |
| (69) | (αS)-3,4-dihydro-6-[(1E)-3-[(4-methyl-2-pyridinyl)amino]-1-propenyl]-4-oxo-α-[[(phenylmethoxy)carbonyl]amino]-2-quinazolinepropanoic acid | 514 |
| (70) | (αS)-3,4-dihydro-4-oxo-6-[(1E)-3-[[[(phenylmethyl)amino]carbonyl]amino]-1-propenyl]-α-[[(phenylmethyl)sulfonyl]amino]-2-quinazolinepropanoic acid | 576 |
| (71) | α-[[(1,1-dimethylethoxy)carbonyl]amino]-(αS)-3,4-dihydro-4-oxo-6-[(1E)-3-[(3,4,5,6-tetrahydro-2H-azepin-7-yl)amino]-1-propenyl]-2-quinazolinepropanoic acid | 484 |
| (72) | (αS)-3,4-dihydro-4-oxo-6-[(1E)-3-[[[(phenylmethyl)amino]carbonyl]amino]-1-propenyl]-α-[(2-thienylsulfonyl)amino]-2-quinazolinepropanoic acid | 568 |
| (73) | α-[(butylsulfonyl)amino]-(αS)-3,4-dihydro-4-oxo-6-[(1E)-3-[[[(phenylmethyl)amino]carbonyl]amino]-1-propenyl]-2-quinazolinepropanoic acid | 542 |
| (74) | (αS)-3,4-dihydro-4-oxo-α-[[(2,3,4,5,6-pentamethylphenyl)sulfonyl]amino]-6-[(1E)-3-[(3,4,5,6-tetrahydro-2H-azepin-7-yl)amino]-1-propenyl]-2-quinazolinepropanoic acid | 594 |
| (75) | 6-[(1E)-3-[[(cyclohexylamino)carbonyl]amino]-1-propenyl]-(αS)-3,4-dihydro-4-oxo-α-[[(2,3,4,5,6-pentamethylphenyl)sulfonyl]amino]-2-quinazolinepropanoic acid | 624 |
| (76) | (αS)-3,4-dihydro-α-[[[2-(1-naphthalenyl)ethyl]sulfonyl]amino]-4-oxo-6-[(1E)-3-[[[(phenylmethyl)amino]carbonyl]amino]-1-propenyl]-2-quinazolinepropanoic acid | 640 |
| (77) | (αS)-3,4-dihydro-α-[[(4-methoxyphenoxy)carbonyl]amino]-4-oxo-6-[(1E)-3-[[[(phenylmethyl)amino]carbonyl]amino]-1-propenyl]-2-quinazolinepropanoic acid | 572 |
| (78) | (βR,S)-3,4-dihydro-3-methyl-4-oxo-β-phenyl-6-[(1E)-3-[(4,5-dihydro-1H-imidazol-2-yl)amino]-1-propenyl]-2-quinazolinepropanoic acid | 432 |
| (79) | 6-[(E)-2-[[(cyclohexylamino)carbonyl]amino]-1-methylethenyl]-(αS)-3,4-dihydro-4-oxo-α-[[(2,3,4,5,6-pentamethylphenyl)sulfonyl]amino]-2-quinazolinepropanoic acid | 624 |
| (80) | (αS)-3,4-dihydro-4-oxo-α-[[(2,3,4,5,6-pentamethylphenyl)sulfonyl]amino]-6-[(1E)-3-[[[(2-phenylethyl)amino]carbonyl]amino]-1-propenyl]-2-quinazolinepropanoic acid | 646 |
| (81) | (αS)-3,4-dihydro-6-[(1E)-3-[(4-methyl-2-oxazolyl)amino]-1-propenyl]-4-oxo-α-[[(2,3,4,5,6-pentamethylphenyl)sulfonyl]amino]-2-quinazolinepropanoic acid | 580 |
| (82) | 3,4-dihydro-4-oxo-3-(phenylmethyl)-6-[(1E)-3-(2-pyridinylamino)-1-propenyl]-2-quinazolinepropanoic acid | 441 |

EXAMPLE 83

As a specific embodiment of an oral composition, 100 mg of the Compound 1 of Example 1 is formulated with sufficient finely divided lactose to provide a total amount of 580 to 590 mg to fill a size O hard gel capsule.

Biological Experimental Examples

As demonstrated by the results of the biological studies described hereinafter and shown in Table 2, the compounds of the present invention block vitronectin by binding to isolated αvβ3 (demonstrating $IC_{50}$ values of from about 1 to about 300 nM) and inhibit fibrinogen by binding to isolated GPIIb/IIIa as well. The compounds of the present invention inhibit integrin-mediated cell-cell or cell-matrix adhesion and, therefore, may be useful in treating integrin mediated disorders including, but not limited to, restenosis, thrombosis, inflammation, atherosclerosis, arthritis, angiogenesis, osteoporosis, bone resorption, tumor cell metastasis, tumor growth, macular degeneration, diabetic retinopathy, diseases of the lung/airway (D. Cox, *Drug News & Perspectives* 1995, 8, 197).

In vitro Solid Phase Purified αvβ3 Binding Assay

The vitronectin/αvβ3 binding assay methods were derived from Mehta et al. (*Biochem J.* 1998, 330, 861). Human αvβ3 (Chemicon International Inc., Temecula, Calif.), at a concentration of 1 μg/ml dissolved in Tris buffer (20 mM Tris, 1 mM CaCl$_2$, 1 mM MgCl$_2$, 10 μM MnCl$_2$, 150 mM NaCl), was immobilized on Immulon 96 well plates (Dynex Technologies, Chantilly, Va.) overnight at 4° C. Plates were washed and treated with blocking buffer (3% BSA in Tris buffer) for 2 h at 37 C. Plates were then rinsed 2 times in Tris buffer containing 0.3% BSA and 0.2% Tween20 (polyoxyethylenesorbitan monolaurate). Five minutes prior to the addition of 5 nM vitronectin (Sigma, St. Louis, Mo.), compounds of the invention were added to wells in duplicate. Each plate included c-RGDfV as an internal control. Following a 3 hour incubation at 37° C., plates were washed 5 times in assay buffer. An anti-human vitronectin IgG rabbit polyclonal antibody (Calbiochem, San Diego, Calif.) was added (1:2000) and plates were incubated for 1 hour at room temperature. VectaStain ABC peroxidase kit reagents (Vector Laboratories, Burlingame, Calif.) employing a biotin labeled anti-rabbit IgG, were utilized for detection of bound antibody. Plates were read at 490 nm on a Molecular Devices (Sunnyvale, Calif.) microplate reader.

In vitro Solid Phase Purified Glycoprotein IIb/IIIa Binding Assay

A 96 well Immulon-2 microtiter plate (Dynatech-Immulon) was coated with 50 μl/well of RGD-affinity purified GPIIb/IIIa (effective range 0.5–10 μg/mL) in 10 mM HEPES, 150 mM NaCl, 1 mM $MgCl_2$ at pH 7.4. The plate was covered and incubated overnight at 4° C. The GPIIb/IIIa solution was discarded and 150 μl of 5% BSA was added and incubated at RT for 1–3 h. The plate was washed extensively with modified Tyrodes buffer. Biotinylated fibrinogen (25 μl/well) at 2× final concentration was added to the wells that contain the test compounds (25 μl/well). The plate was covered and incubated at RT for 2–4 h. Twenty minutes prior to incubation completion, one drop of Reagent A (VectaStain ABC Horse Radish Peroxidase kit, Vector Laboratories, Inc.) and one drop Reagent B were added with mixing to 5 mL modified Tyrodes buffer mix and let stand. The ligand solution was discarded and the plate washed (5×200 μl/well) with modified Tyrodes buffer. Vecta Stain HRP-Biotin-Avidin reagent (50 μl/well, as prepared above) was added and incubated at RT for 15 min. The Vecta Stain solution was discarded and the wells washed (5×200 μl/well) with modified Tyrodes buffer. Developing buffer (10 mL of 50 mM citrate/phosphate buffer @ pH 5.3, 6 mg o-phenylenediamine, 6 μl 30% $H_2O_2$; 50 μl/well) was added and incubated at rt for 3–5 min, and then 2 N $H_2SO_4$ (50 μl/well) was added. The absorbance was read at 490 nM.

TABLE 2

In Vitro Results

| Cpd# | αvβ3 Binding $IC_{50}(\mu M)$ | GPIIb/IIIa Binding $IC_{50}(\mu M)$ |
|---|---|---|
| 1 | 0.00075 | 0.024 |
| 1a | 0.0034 | 0.029 |
| 2 | 0.055 | 0.56 |
| 3 | 0.0032 | 0.078 |
| 4 | 0.014 | 0.32 |
| 5 | 0.0086 | 0.67 |
| 6 | 0.0053 | 0.041 |
| 7 | 0.0070 | 0.33 |
| 8 | 0.21 | 0.58 |
| 9 | >5 | 0.088 |
| 10 | 0.0061 | 0.64 |
| 11 | 0.0096 | 0.64 |
| 12 | >0.5 | 18 |
| 13 | 0.14 | 1.7 |
| 14 | 0.025 | 1.8 |
| 15 | 0.018 | 0.077 |
| 16 | 0.268 | 0.036 |
| 17 | >50 | 18 |
| 18 | 18 | >50 |
| 19 | >5 | 0.45 |
| 20 | >5 | 0.66 |
| 21 | >0.05 | 1.6 |
| 22 | >0.5 | 1.2 |
| 23 | 0.30 | 6.4 |
| 24 | 0.023 | 1.4 |
| 25 | 0.072 | 9.6 |
| 26 | 0.015 | 1.3 |
| 27 | 0.12 | 0.019 |
| 28 | >0.3 | 2.2 |
| 29 | 0.038 | 0.24 |
| 30 | 0.20 | 0.083 |
| 31 | 0.070 | 1.8 |
| 32 | 0.021 | 3.9 |
| 33 | 0.013 | 1.1 |
| 34 | 0.083 | 1.6 |
| 35 | 0.059 | 4.8 |
| 36 | 0.025 | 2.7 |
| 37 | 0.054 | 0.70 |
| 38 | 1.4 | 0.22 |
| 39 | 1.8 | 1.8 |
| 40 | 0.74 | 1.9 |
| 41 | 0.019 | 0.24 |
| 42 | 0.0054 | 0.060 |
| 43 | 0.022 | 0.88 |
| 44 | 0.024 | 0.79 |
| 45 | 0.015 | 1.8 |
| 46 | 0.0058 | 0.74 |
| 47 | 0.132 | 0.096 |
| 48 | 0.011 | 0.064 |
| 49 | 0.0088 | 0.82 |
| 50 | 0.0068 | 0.051 |
| 51 | 0.017 | 4.8 |
| 52 | 0.024 | 0.11 |
| 53 | 0.031 | 0.20 |
| 54 | 0.038 | 5.0 |
| 55 | 0.042 | 0.27 |
| 56 | 0.032 | 3.9 |
| 57 | 0.043 | 3.7 |
| 58 | 0.044 | 2.5 |
| 59 | 0.059 | 3.9 |
| 60 | 0.058 | 0.62 |
| 61 | 0.069 | 12 |
| 62 | 0.079 | 4.1 |
| 63 | 0.10 | 0.95 |
| 64 | 0.15 | 1.1 |
| 65 | 0.16 | 4.1 |
| 66 | 0.21 | 0.78 |
| 67 | 0.42 | 0.58 |
| 68 | 0.44 | 0.23 |
| 69 | 0.49 | 18 |
| 70 | 0.55 | 3.2 |
| 71 | 0.96 | 12 |
| 72 | 1.3 | 17 |
| 73 | 2.0 | >50 |
| 74 | 5.4 | 1.3 |
| 75 | 0.62 | 4.9 |
| 76 | >0.5 | 45 |
| 77 | >0.5 | 46 |
| 78 | 5.4 | 55 |
| 79 | >0.5 | 7.3 |
| 80 | 0.050 | 2.7 |
| 81 | >5 | 7.1 |
| 82 | >5 | >50 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of Formula (I):

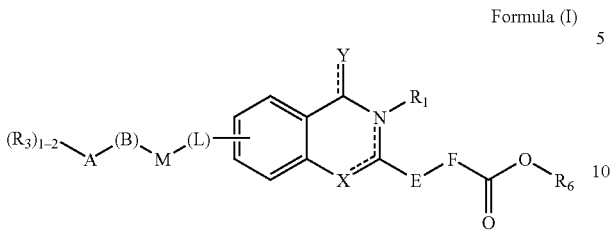

Formula (I)

wherein
A is selected from the group consisting of carbonyl, amino, carbamoyl, acetamido, acetimido, amidino, iminomethylamino, ureido, biureto, biurea, thioureido, guanidino, biguanido, biguanidino, amidrazone, hydrazo, carbazoyl, semicarbazido, cycloalkylene, heterocyclene, arylene and heteroarylene; wherein arylene and heteroarylene are optionally substituted with one to two additional substituents independently selected from the group consisting of $C_1$–$C_8$ alkyl, $C_1$–$C_8$ alkoxy, halogen, (halo)$_{1-3}$($C_1$–$C_8$)alkyl and (halo)$_{1-3}$($C_1$–$C_8$)alkoxy;

(B) is optionally present and is selected from the group consisting of NH, O and C(O);

M is selected from the group consisting of $C_1$–$C_6$ alkylene, $C_2$–$C_6$ alkenylene, $C_2$–$C_6$ alkynylene and arylene; wherein arylene is optionally substituted with one to four additional substituents independently selected from the group consisting of $C_1$–$C_8$ alkyl, $C_1$–$C_8$ alkoxy, halogen, (halo)$_{1-3}$($C_1$–$C_8$)alkyl and (halo)$_{1-3}$($C_1$–$C_8$)alkoxy;

$R_3$ is one to two substituents independently selected from the group consisting of hydrogen, $C_1$–$C_8$ alkyl, cycloalkyl, heterocyclo, aryl, aryl($C_1$–$C_8$)alkyl, heteroaryl, heteroaryl($C_1$–$C_8$)alkyl, amino, $C_1$–$C_8$ alkylamino, imino, iminomethyl, amidino, $C_1$–$C_8$ alkylamidino, di($C_1$–$C_8$)alkylamidino, cycloalkylamidino, halogen and hydroxy; wherein cycloalkyl, heterocyclo, aryl, heteroaryl and the aryl and heteroaryl portions of arylalkyl and heteroarylalkyl are optionally substituted with one to two substituents independently selected from the group consisting of $C_1$–$C_8$ alkyl, $C_1$–$C_8$ alkoxy, aryl and halogen; and, wherein heterocyclo is optionally substituted with a substituent selected from oxo;

(L) is optionally present and is selected from the group consisting of NH, O, S and C(O);

Y is selected from the group consisting of two substituents joined to the ring by single-bonds and one substituent joined to the ring by a double-bond; wherein the two substituents joined to the ring by single-bonds are independently selected from the group consisting of hydrogen, $C_1$–$C_8$ alkyl, $C_1$–$C_8$ alkoxy, halogen, (halo)$_{1-3}$($C_1$–$C_4$)alkyl and (halo)$_{1-3}$($C_1$–$C_4$)alkoxy; alternatively, the two substituents are taken together to form a moiety selected from the group consisting of cycloalkyl and —O—(CH$_2$)$_{1-4}$—O—; and, wherein the one substituent joined to the ring by a double-bond is selected from the group consisting of S, O, $C_1$–$C_8$ alkylidene, (halo)$_{1-2}$methylene, and (halo)$_{1-3}$($C_2$–$C_4$) alkylidene;

X is N or NH;

$R_1$ is optionally present and is selected from the group consisting of hydrogen, $C_1$–$C_8$ alkyl, cycloalkyl, cycloalkyl($C_1$–$C_6$)alkyl, aryl, aryl($C_1$–$C_6$)alkyl, heteroaryl, heteroaryl($C_1$–$C_6$)alkyl, arylamino and heteroarylamino; wherein aryl, heteroaryl and the aryl and heteroaryl portions of arylalkyl and heteroarylalkyl are optionally substituted with one to five substituents independently selected from the group consisting of $C_1$–$C_8$ alkyl, $C_1$–$C_8$ alkoxy, aryl, aryl($C_1$–$C_8$)alkyl, heteroaryl, amino, $C_1$–$C_8$ alkylamino, di($C_1$–$C_8$ alkyl)amino, heteroarylamino, imino, iminomethyl, sulfonyl, halogen, hydroxy, nitro, cyano, (halo)$_{1-3}$($C_1$–$C_4$)alkyl and (halo)$_{1-3}$($C_1$–$C_4$)alkoxy;

E is $C_1$–$C_4$ alkyl substituted with W and W';

F is $C_1$–$C_4$ alkyl substituted with U and U';

W, W', U and U' are independently selected from the group consisting of hydrogen, $C_1$–$C_8$ alkyl, $C_2$–$C_8$ alkenyl, $C_2$–$C_8$ alkynyl, cycloalkyl, cycloalkyl($C_1$–$C_4$)alkyl, heterocyclo, heterocyclo($C_1$–$C_4$)alkyl, aryl, aryl ($C_1$–$C_4$)alkyl, biaryl, heteroaryl, heteroaryl($C_1$–$C_4$) alkyl, —N[($R_4$),T($R_5$)] and halogen; wherein heterocyclo, aryl, biaryl, heteroaryl and the heterocyclo, aryl and heteroaryl portions of heterocycloalkyl, arylalkyl and heteroarylalkyl are optionally substituted with one to five substituents independently selected from the group consisting of $C_1$–$C_4$ alkyl, $C_1$–$C_4$ alkoxy, amino, $C_1$–$C_4$ alkylamino, di($C_1$–$C_4$ alkyl) amino, halogen, hydroxy, nitro and cyano; and, alternatively, two optional substituents on aryl, heteroaryl and the aryl and heteroaryl portions of arylalkyl and heteroarylalkyl are taken together to form a moiety selected from the group consisting of cycloalkyl, heterocyclo and —O—(CH$_2$)$_{1-4}$—O—; with the proviso that if one of W, W', U and U' are selected from —N[($R_4$),T($R_5$)], then the remaining W, W', U and U' cannot be selected from —N[($R_4$),T($R_5$)];

$R_4$ is selected from the group consisting of hydrogen and $C_1$–$C_8$ alkyl;

T is selected from the group consisting of arylene, carbonyl, carboxyl, sulfonyl and —C(O)NH—; wherein arylene is optionally substituted with one to two additional substituents independently selected from the group consisting of $C_1$–$C_4$ alkyl, $C_1$–$C_4$ alkoxy and halogen;

$R_5$ is selected from the group consisting of hydrogen, $C_1$–$C_8$ alkyl, $C_2$–$C_8$ alkenyl, cycloalkyl, heterocyclo, aryl, aryl($C_1$–$C_4$)alkyl, aryl($C_2$–$C_4$ )alkenyl, biaryl, biaryl($C_1$–$C_4$)alkyl, heteroaryl, heteroaryl($C_1$–$C_4$)alkyl and amino; wherein heterocyclo, aryl, heteroaryl and the aryl and heteroaryl portions of arylalkyl, arylalkenyl, biaryl, biarylalkyl and heteroarylalkyl are optionally substituted with one to five substituents independently selected from the group consisting of $C_1$–$C_4$ alkyl, $C_1$–$C_4$ alkoxy, heterocyclo, aryl, aryl($C_1$–$C_4$) alkyl, arylsulfonyl, heteroaryl, amino, $C_1$–$C_4$ alkylamino, di($C_1$–$C_4$ alkyl)amino, halogen, hydroxy, (halo)$_{1-3}$($C_1$–$C_4$)alkyl and (halo)$_{1-3}$($C_1$–$C_4$)alkoxy; and, alternatively, two optional substituents on aryl, heteroaryl and the aryl and heteroaryl portions of arylalkyl, arylalkenyl and heteroarylalkyl are taken together to form a moiety selected from the group consisting of cycloalkyl, heterocyclo and —O—(CH$_2$)$_{1-4}$—O—;

$R_6$ is selected from the group consisting of hydrogen, $C_1$–$C_8$ alkyl and (CH$_2$)$_{1-8}$CON($R_7$)$_2$; and, $R_7$ is selected from the group consisting of hydrogen, $C_1$–$C_8$ alkyl and cycloalkyl;

or a pharmaceutically acceptable racemate, enantiomer, diastereomer, or salt thereof.

2. The compound of claim 1 wherein A is selected from the group consisting of carbonyl, amino, carbamoyl, amidino, iminomethylamino, ureido, guanidino, heterocyclene and heteroarylene; wherein heteroarylene is optionally substituted with one to two additional substituents independently selected from the group consisting of $C_1$–$C_4$ alkyl, $C_1$–$C_4$ alkoxy, halogen, $(halo)_{1-3}(C_1$–$C_4)$alkyl and $(halo)_{1-3}(C_1$–$C_4)$alkoxy.

3. The compound of claim 1 wherein A is selected from the group consisting of amino, amidino, iminomethylamino, ureido, guanidino, heterocyclene and heteroarylene; wherein heteroarylene is optionally substituted with one to two additional substituents independently selected from the group consisting of $C_1$–$C_4$ alkyl, $C_1$–$C_4$ alkoxy, halogen, $(halo)_{1-3}(C_1$–$C_4)$alkyl and $(halo)_{1-3}(C_1$–$C_4)$alkoxy.

4. The compound of claim 1 wherein A is selected from the group consisting of amino, iminomethylamino, ureido, guanidino, pyrrolidinylene and pyridinylene; wherein pyridinylene is optionally substituted with one to two additional substituents independently selected from the group consisting of methyl, ethyl, n-propyl, i-propyl, n-butyl, t-butyl, methoxy, ethoxy, propoxy, chlorine, fluorine, bromine, trifluoromethyl and trifluoromethoxy.

5. The compound of claim 1 wherein (B) is optionally present and is selected from the group consisting of O and C(O).

6. The compound of claim 1 wherein (B) is optionally present and is O.

7. The compound of claim 1 wherein M is selected from the group consisting of —$CH_2$—, —$(CH_2)_2$—, —$(CH_2)_3$—, —$(CH_2)_4$—, —$(CH_2)_5$—, —$C(CH_3)_2$—, —$CH(CH_3)$—$CH_2$—, —$CH_2$—$CH(CH_3)$—, —$CH(CH_3)$—$(CH_2)_2$—, —$(CH_2)_2$—$CH(CH_3)$—, —$C(CH_3)_2$—$CH_2$—, —$CH_2$—$C(CH_3)_2$—, —CH=CH—, —CH=CH—$CH_2$—, —$CH_2$—CH=CH—, —$CH_2$—C(=$CH_2$)—, —CH=C($CH_3$)—, —C($CH_3$)=CH—, —CH=CH—$(CH_2)_2$—, —$CH_2$—CH=CH—$CH_2$—, —$(CH_2)_2$—CH=CH—, —CH($CH_3$)—CH=CH—, —C≡C—, —C≡C—$CH_2$—, —$CH_2$—C≡C—, —C≡C—$(CH_2)_2$—, —$(CH_2)_2$—C≡C— and -Ph-; wherein phenylene is optionally substituted with one to four additional substituents independently selected from the group consisting of $C_1$–$C_4$ alkyl, $C_1$–$C_4$ alkoxy, halogen, $(halo)_{1-3}(C_1$–$C_4)$alkyl and $(halo)_{1-3}(C_1$–$C_4)$alkoxy.

8. The compound of claim 1 wherein M is selected from the group consisting of —$(CH_2)_2$—, —$(CH_2)_3$—, —$(CH_2)_4$—, —$C(CH_3)_2$—, —$CH(CH_3)$—$(CH_2)_2$—, —$C(CH_3)_2$—$CH_2$—, —CH=CH—, —CH=CH—$CH_2$—, —$CH_2$—CH=CH—, $CH_2$—$CH_2$—C(=$CH_2$)—, —CH=C($CH_3$)—, —C($CH_3$)=CH—, —CH=CH—$(CH_2)_2$—, —$CH_2$—CH=CH—$CH_2$—, —$(CH_2)_2$—CH=CH—, —CH($CH_3$)—CH=CH—, —C≡C—, —C≡C—$CH_2$—, —$CH_2$—C≡C—, —C≡C—$(CH_2)_2$—, —$(CH_2)_2$—C≡C— and -Ph-; wherein phenylene is optionally substituted with one to four additional substituents independently selected from the group consisting of $C_1$–$C_4$ alkyl, $C_1$–$C_4$ alkoxy, halogen, $(halo)_{1-3}(C_1$–$C_4)$alkyl and $(halo)_{1-3}(C_1$–$C_4)$alkoxy.

9. The compound of claim 1 wherein M is selected from the group consisting of —$(CH_2)_2$—, —$(CH_2)_3$—, —CH=CH—, —$CH_2$—CH=CH—, —$CH_2$—C(=$CH_2$)—, —CH=C($CH_3$)—, —$(CH_2)_2$—CH=CH—, —C≡C—, —$CH_2$—C≡C—, —$(CH_2)_2$—C≡C— and -Ph-; wherein phenylene is optionally substituted with one to four additional substituents independently selected from the group consisting of methyl, ethyl, n-propyl, i-propyl, n-butyl, t-butyl, methoxy, ethoxy, propoxy, chlorine, fluorine, bromine, trifluoromethyl and trifluoromethoxy.

10. The compound of claim 1 wherein $R_3$ is one to two substituents independently selected from the group consisting of hydrogen, $C_1$–$C_8$ alkyl, cycloalkyl, heterocyclo, aryl, aryl($C_1$–$C_8$)alkyl, heteroaryl, amino, ($C_1$–$C_8$ alkyl)amino, imino, amidino and halogen; wherein cycloalkyl and heteroaryl are optionally substituted with one to two substituents independently selected from the group consisting of $C_1$–$C_4$ alkyl, $C_1$–$C_4$ alkoxy and halogen; and, wherein heterocyclo is optionally substituted with a substituent selected from oxo.

11. The compound of claim 1 wherein $R_3$ is one to two substituents independently selected from the group consisting of hydrogen, $C_1$–$C_4$ alkyl, cycloalkyl, heterocyclo, aryl, aryl($C_1$–$C_4$)alkyl, heteroaryl, amino, ($C_1$–$C_4$ alkyl)amino, imino and amidino; wherein cycloalkyl and heteroaryl are optionally substituted with one to two substituents independently selected from the group consisting of methyl, ethyl, n-propyl, i-propyl, n-butyl, t-butyl, methoxy, ethoxy, propoxy, chlorine, fluorine, bromine; and, wherein heterocyclo is optionally substituted with a substituent selected from oxo.

12. The compound of claim 1 wherein $R_3$ is one to two substituents independently selected from the group consisting of hydrogen, methyl, ethyl, n-propyl, i-propyl, n-butyl, cyclopropyl, cyclohexyl, 3,4-dihydro-2H-pyrrolyl, pyrrolidinyl, 4,5-dihydro-1H-imidazolyl, 3,4,5,6-tetrahydro-pyridinyl, 3,4-dihydro-quinazolinyl, 3,4,5,6-tetrahydro-2H-azepinyl, 3,4,5,6,7,8-hexahydro-azocinyl, phenyl, benzyl, phenethyl, oxazolyl, imidazolyl, pyridinyl, amino, methylamino, ethylamino, imino and amidino; wherein cyclopropyl, oxazolyl, imidazolyl and pyridinyl are optionally substituted with one to two substituents independently selected from the group consisting of methyl and chlorine; and, wherein 3,4-dihydro-quinazolinyl is optionally substituted with a substituent selected from oxo.

13. The compound of claim 1 wherein (L) is optionally present and is O.

14. The compound of claim 1 wherein (L) is not present.

15. The compound of claim 1 wherein Y is selected from the group consisting of two substituents joined to the ring by single-bonds and one substituent joined to the ring by a double-bond; wherein the two substituents joined to the ring by single-bonds are independently selected from the group consisting of hydrogen, $C_1$–$C_4$ alkyl, $C_1$–$C_4$ alkoxy, halogen, $(halo)_{1-3}(C_1$–$C_4)$alkyl and $(halo)_{1-3}(C_1$–$C_4)$alkoxy; and, wherein the one substituent joined to the ring by a double-bond is selected from the group consisting of S, O, $C_1$–$C_4$ alkylidene, and $(halo)_2$methylene.

16. The compound of claim 1 wherein Y is one substituent joined to the ring by a double-bond selected from the group consisting of S, O, methylene, ethylidene, and difluoromethylene.

17. The compound of claim 1 wherein Y is one substituent joined to the ring by a double-bond selected from O.

18. The compound of claim 1 wherein X is N.

19. The compound of claim 1 wherein $R_1$ is selected from the group consisting of hydrogen, $C_1$–$C_4$ alkyl, aryl and aryl($C_1$–$C_4$)alkyl; wherein aryl and the aryl portion of arylalkyl are optionally substituted with one to five substituents independently selected from the group consisting of $C_1$–$C_4$ alkyl, $C_1$–$C_4$ alkoxy, aryl, aryl($C_1$–$C_4$)alkyl, heteroaryl, amino, $C_1$–$C_4$ alkylamino, di($C_1$–$C_4$ alkyl)amino, heteroarylamino, imino, iminomethyl, sulfonyl, halogen, hydroxy, nitro, cyano, $(halo)_{1-3}(C_1$–$C_4)$alkyl and $(halo)_{1-3}(C_1$–$C_4)$alkoxy.

20. The compound of claim 1 wherein $R_1$ is selected from the group consisting of hydrogen, methyl, ethyl, n-propyl, n-butyl, t-butyl, phenyl, naphthalenyl, benzyl and phenethyl.

21. The compound of claim 1 wherein $R_1$ is selected from the group consisting of hydrogen, methyl, ethyl, n-propyl and benzyl.

22. The compound of claim 1 wherein E is selected from the group consisting of —C(W,W')—, —C(W,W')—CH$_2$—, —CH(W)—CH(W')— and —CH$_2$—C(W,W')—.

23. The compound of claim 1 wherein E is selected from —C(W,W')—.

24. The compound of claim 1 wherein F is selected from the group consisting of —C(U,U')—, —C(U,U')—CH$_2$—, —CH(U)—CH(U')— and —CH$_2$—C(U,U')—.

25. The compound of claim 1 wherein F is selected from the group consisting of —C(U,U')—CH$_2$— and —C(U,U')—.

26. The compound of claim 1 wherein F is selected from —C(U,U')—.

27. The compound of claim 1 wherein W, W', U and U' are independently selected from the group consisting of hydrogen, $C_1$–$C_4$ alkyl, $C_2$–$C_4$ alkenyl, $C_2$–$C_4$ alkynyl, heterocyclo, aryl, aryl($C_1$–$C_4$)alkyl, heteroaryl, —N[($R_4$),T($R_5$)] and halogen; wherein heterocyclo, aryl, heteroaryl and the aryl portion of arylalkyl are optionally substituted with one to five substituents independently selected from the group consisting of $C_1$–$C_4$ alkyl, $C_1$–$C_4$ alkoxy, amino, $C_1$–$C_4$ alkylamino, di($C_1$–$C_4$alkyl)amino, halogen, hydroxy, nitro and cyano; and, alternatively, two optional substituents on aryl, heteroaryl and the aryl portion of arylalkyl are taken together to form a moiety selected from —O—(CH$_2$)$_{1-4}$—O—; with the proviso that if one of W, W', U and U' are selected from —N[($R_4$),T($R_5$)], then the remaining W, W', U and U' cannot be selected from —N[($R_4$),T($R_5$)].

28. The compound of claim 1 wherein W, W', U and U' are independently selected from the group consisting of hydrogen, heterocyclo, aryl, aryl($C_1$–$C_4$)alkyl, heteroaryl and —N[($R_4$),T($R_5$)]; wherein aryl, heteroaryl and the aryl portion of arylalkyl are optionally substituted with one to five substituents independently selected from the group consisting of $C_1$–$C_4$ alkyl, $C_1$–$C_4$ alkoxy, halogen and hydroxy; and, alternatively, two optional substituents on aryl are taken together to form a moiety selected from —O—(CH$_2$)$_{1-4}$—O—; with the proviso that if one of W, W', U and U' are selected from —N[($R_4$),T($R_5$)], then the remaining W, W', U and U' cannot be selected from —N[($R_4$),T($R_5$)].

29. The compound of claim 1 wherein W, W', U and U' are independently selected from the group consisting of hydrogen and —N[($R_4$),T($R_5$)]; with the proviso that if one of W, W', U and U' are selected from —N[($R_4$),T($R_5$)], then the remaining W, W', U and U' cannot be selected from —N[($R_4$),T($R_5$)].

30. The compound of claim 1 wherein $R_4$ is selected from the group consisting of hydrogen and $C_1$–$C_4$ alkyl.

31. The compound of claim 1 wherein $R_4$ is selected from the group consisting of hydrogen, methyl, ethyl, n-propyl, i-propyl, n-butyl and t-butyl.

32. The compound of claim 1 wherein $R_4$ is hydrogen.

33. The compound of claim 1 wherein T is selected from the group consisting of carbonyl, carboxyl, sulfonyl and —C(O)NH—.

34. The compound of claim 1 wherein T is selected from the group consisting of carboxyl, sulfonyl and —C(O)NH—.

35. The compound of claim 1 wherein $R_5$ is selected from the group consisting of hydrogen, $C_1$–$C_4$ alkyl, $C_2$–$C_4$ alkenyl, aryl, aryl($C_1$–$C_4$)alkyl, aryl($C_2$–$C_4$)alkenyl, heteroaryl and amino; wherein aryl, heteroaryl and the aryl portion of arylalkyl and arylalkenyl are optionally substituted with one to five substituents independently selected from the group consisting of $C_1$–$C_4$ alkyl, $C_1$–$C_4$ alkoxy, arylsulfonyl, heteroaryl, di($C_1$–$C_4$ alkyl)amino, halogen, trifluoro($C_1$–$C_4$) alkyl and trifluoro($C_1$–$C_4$)alkoxy; and, alternatively, two optional substituents on aryl and the aryl portion of arylalkyl and arylalkenyl are taken together to form a moiety selected from —O—(CH$_2$)$_{1-4}$—O—.

36. The compound of claim 1 wherein $R_5$ is selected from the group consisting of methyl, ethyl, n-propyl, i-propyl, n-butyl, t-butyl, ethenyl, propenyl, phenyl, naphthalenyl, benzyl, naphthalenethyl, phenethenyl, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, quinolinyl, isoquinolinyl and amino; wherein phenyl, naphthalenyl, furyl, thienyl, pyrrolyl, oxazolyl, thiazolyl, imidazolyl, pyrazolyl, isoxazolyl, isothazolyl, pyridinyl, pyridazinyl, pyrimidinyl, pyrazinyl, quinolinyl, isoquinolinyl and the phenyl portion of benzyl and phenethenyl are optionally substituted with one to five substituents independently selected from the group consisting of methyl, ethyl, i-propyl, n-propyl, n-butyl, t-butyl, methoxy, ethoxy, propoxy, phenylsulfonyl, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, N,N-dimethylamino, N,N-diethylamino, chlorine, fluorine, trifluoromethyl and trifluoromethoxy; and, alternatively, two optional substituents on phenyl and the phenyl portion of benzyl and phenethenyl are taken together to form a moiety selected from —O—(CH$_2$)$_{1-4}$—O—.

37. The compound of claim 1 wherein $R_5$ is selected from the group consisting of n-butyl, t-butyl, phenyl, naphthalenyl, benzyl, naphthalenethyl, phenethenyl, thienyl, pyrazolyl, isoxazolyl and quinolinyl; wherein phenyl, naphthalenyl, thienyl, pyrazolyl, isoxazolyl and the phenyl portion of benzyl and phenethenyl are optionally substituted with one to five substituents independently selected from the group consisting of methyl, t-butyl, methoxy, phenylsulfonyl, isoxazolyl, pyridinyl, N,N-dimethylamino, chlorine, trifluoromethyl and trifluoromethoxy; and, alternatively, two optional substituents on phenyl and the phenyl portion of benzyl and phenethenyl are taken together to form a moiety selected from —O—(CH$_2$)—O—.

38. The compound of claim 1 wherein $R_6$ is selected from the group consisting of hydrogen, $C_1$–$C_4$ alkyl, and (CH$_2$)$_{1-4}$CON($R_7$)$_2$.

39. The compound of claim 1 wherein $R_6$ is selected from the group consisting of hydrogen, methyl, ethyl, n-propyl, and CH$_2$CON($R_7$)$_2$.

40. The compound of claim 1 wherein $R_6$ is selected from the group consisting of hydrogen and methyl.

41. The compound of claim 1 wherein $R_7$ is selected from the group consisting of hydrogen and $C_1$–$C_4$ alkyl.

42. The compound of claim 1 wherein $R_7$ is selected from the group consisting of hydrogen and methyl.

43. The compound of claim 1 wherein the compound of Formula (I) is a compound of Formula (Ia):

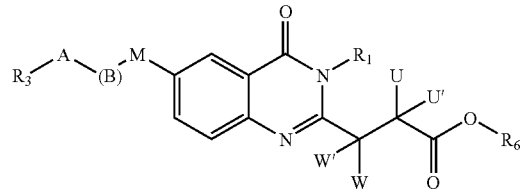

Formula (Ia)

wherein R₃, A, (B), M, W, W', U, U', R₁ and R₆ are dependently selected from the group consisting of

| R₃ | A | (B) M | W, W' | U, U' | R₁ | R₆ |
|---|---|---|---|---|---|---|
| 4,5-dihydro-1H-imidazol-2-yl | NH | — CH₂(CH)₂ | H, H | (Me₅)PhSO₂NH, H | H | H; |
| 4,5-dihydro-1H-imidazol-2-yl | NH | — CH₂(CH)₂ | H, H | (Me₅)PhSO₂NH, H | H | Na; |
| 4,5-dihydro-1H-imidazol-2-yl | NH | — CH₂(CH)₂ | H, H | PhCH₂OC(O)NH, H | H | H; |
| 4,5-dihydro-1H-imidazol-2-yl | NH | — CH₂(CH)₂ | H, H | 2,4,6-Me₃Ph SO₂NH, H | H | H; |
| 4,5-dihydro-1H-imidazol-2-yl | NH | — CH₂(CH)₂ | H, H | 8-quinolinyl SO₂NH, H | H | H; |
| 4,5-dihydro-1H-imidazol-2-yl | NH | — CH₂(CH)₂ | H, H | 1-naphthalenyl (CH₂)₂SO₂NH, H | H | H; |
| 4,5-dihydro-1H-imidazol-2-yl | NH | — CH₂(CH)₂ | H, H | 5-(2-pyridinyl)-2-thienylSO₂NH, H | H | H; |
| 4,5-dihydro-1H-imidazol-2-yl | NH | — CH₂(CH)₂ | H, H | PhCH₂SO₂NH, H | H | H; |
| 4,5-dihydro-1H-imidazol-2-yl | NH | — (CH₂)₂(CH)₂ | H, H | PhCH₂OC(O)NH, H | H | H; |
| 4,5-dihydro-1H-imidazol-2-yl | NH | — 3-Ph | H, H | PhCH₂OC(O)NH, H | H | H; |
| 2-pyridinyl | NH | — CH₂(CH)₂ | H, H | (Me₅)PhSO₂NH, H | H | H; |
| 2-pyridinyl | NH | — (CH₂)₃ | H, H | (Me₅)PhSO₂NH, H | H | H; |
| 2-pyridinyl | NH | — CH₂(CH)₂ | H, H | PhNHC(O)NH, H | H | H; |
| Ph | NH C(O)NH | — CH₂(CH)₂ | H, H | (Me₅)PhSO₂NH, H | H | H; |
| 2-pyridinyl | NH | — CH₂(CH)₂ | (Me₅)Ph SO₂NH, H | H, H | H | H; |
| 3,4-dihydro-2H-pyrrol-5-yl | NH | — CH₂(CH)₂ | H, H | (Me₅)PhSO₂NH, H | H | H; |
| — | NH₂C(NH)NH | O (CH₂)₂(CH)₂ | H, H | (Me₅)PhSO₂NH, H | H | H; |
| 2-pyridinyl | NH | — CH₂(CH)₂ | (3-MeO)-Ph, H | H, H | H | H |
| 2-pyridinyl | NH | — CH₂(CH)₂ | (3-MeO)-Ph, H | H, H | CH₃ | H |
| H | NH | — CH₂(CH)₂ | H, H | PhCH₂OC(O)NH, H | H | H; |
| 4,5-dihydro-1H-imidazol-2-yl | NH | — CH₂(C)₂ | H, H | PhCH₂OC(O)NH, H | H | H; |
| 4,5-dihydro-1H-imidazol-2-yl | NH | — CH₂(CH)₂ | H, H | 2,4,6-Cl₃PhSO₂NH, H | H | H; |
| 4,5-dihydro-1H-imidazol-2-yl | NH | — CH₂(CH)₂ | H, H | 5-(Me₂N)-1-naphthalenyl-SO₂NH, H | H | H; |
| 2-pyridinyl | NH | — CH₂(CH)₂ | H, H | 4-(t-butyl)PhSO₂NH, H | H | H; |
| 2-pyridinyl | NH | — CH₂(CH)₂ | H, H | 2-naphthalenylSO₂NH, H | H | H; |
| 2-pyridinyl | NH | — CH₂(CH)₂ | H, H | 4-F₃MePhSO₂NH, H | H | H; |
| 2-pyridinyl | NH | — CH₂(CH)₂ | H, H | 4-MeOPhSO₂NH, H | H | H; |
| 2-imino | 1-pyrrolidinyl | — CH₂(CH)₂ | H, H | (Me₅)PhSO₂NH, H | H | H; |
| 2-pyridinyl | NH | — CH₂(CH)₂ | H, H | 5-(PhSO₂)-2-thienylSO₂NH, H | H | H; |
| 2-pyridinyl | NH | — CH₂(CH)₂ | H, H | 2-Cl-6-MePhSO₂NH, H | H | H; |
| 1-Me-1H-imidazol-2-yl | NH | — CH₂(CH)₂ | H, H | (Me₅)PhSO₂NH, H | H | H; |
| 2-pyridinyl | NH | — CH₂(CH)₂ | H, H | 5-(3-isoxazolyl)-2-thienylSO₂NH, H | H | H; |
| 2-pyridinyl | NH | — CH₂(CH)₂ | H, H | 2,5-(MeO)₂PhSO₂NH, H | H | H; |
| 2-pyridinyl | NH | — CH₂(CH)₂ | H, H | 3,4-(MeO)₂PhSO₂NH, H | H | H; |
| 2-pyridinyl | NH | — CH₂(CH)₂ | H, H | 2-thienylSO₂NH, H | H | H; |
| 2-pyridinyl | NH | — CH₂(CH)₂ | H, H | 4-F₃MeOPhSO₂NH, H | H | H; |
| 2-pyridinyl | NH | — CH₂(CH)₂ | H, H | 5-Cl-1,3-Me₂-1H-pyrazol-4-yl SO₂NH, H | H | H; |
| 2-pyridinyl | NH | — CH₂(CH)₂ | H, H | 3,5-Me₂-4-isoxazoyl SO₂NH, H | H | H; |

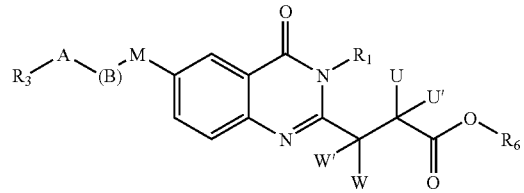

Formula (Ia)

wherein $R_3$, A, (B), M, W, W', U, U', $R_1$ and $R_6$ are dependently selected from the group consisting of

| $R_3$ | A | (B) M | W, W' | U, U' | $R_1$ | $R_6$ |
|---|---|---|---|---|---|---|
| 3-Me-2-pyridinyl | NH | — $CH_2(CH)_2$ | H, H | $(Me_5)PhSO_2NH$, H | H | H; |
| 5-Cl-2-pyridinyl | NH | — $CH_2(CH)_2$ | H, H | $(Me_5)PhSO_2NH$, H | H | H; |
| 5-Cl-2-pyridinyl | NH | — $CH_2(CH)_2$ | H, H | $4\text{-MeOPhSO}_2NH$, H | H | H; |
| 4,5-dihydro-1H-imidazol-2-yl | NH | — $CH_2(CH)_2$ | H, H | $(Me_5)PhSO_2NH$, H | H | $CH_3$; |
| 4,5-dihydro-1H-imidazol-2-yl | NH | — $(CH_2)_2(CH)_2$ | H, H | $(Me_5)PhSO_2NH$, H | H | H; |
| 5-Me-2-pyridinyl | NH | — $CH_2(CH)_2$ | H, H | $(Me_5)PhSO_2NH$, H | H | H; |
| 5-Me-2-pyridinyl | NH | — $CH_2(CH)_2$ | H, H | $3,4\text{-}(MeO)_2PhSO_2NH$, H | H | H; |
| 4-Me-2-pyridinyl | NH | — $CH_2(CH)_2$ | H, H | $(Me_5)PhSO_2NH$, H | H | H; |
| 4-Me-2-pyridinyl | NH | — $CH_2(CH)_2$ | H, H | $3,4\text{-}(MeO)_2PhSO_2NH$, H | H | H; |
| 3-pyridinyl | C(NH)NH | — $CH_2(CH)_2$ | H, H | $(Me_5)PhSO_2NH$, H | H | H; |
| 4,5-dihydro-1H-imidazol-2-yl | NH | — $CH_2(CH)_2$ | H, H | $3,4\text{-}(MeO)_2PhSO_2NH$, H | H | H; |
| benzyl | NHC(O)NH | — $CH_2(CH)_2$ | H, H | $(Me_5)PhSO_2NH$, H | H | H; |
| 4,5-dihydro-1H-imidazol-2-yl | NH | — $CH_2(CH)_2$ | H, H | $4\text{-MeOPhSO}_2NH$, H | H | H; |
| n-butyl | NHC(O)NH | — $CH_2(CH)_2$ | H, H | $(Me_5)PhSO_2NH$, H | H | H; |
| 3,4,5,6-tetrahydro-2-pyridinyl | NH | — $CH_2(CH)_2$ | H, H | $(Me_5)PhSO_2NH$, H | H | H; |
| — | $NH_2 C(O)NH$ | — $CH_2(CH)_2$ | H, H | $(Me_5)PhSO_2NH$, H | H | H; |
| benzyl | NHC(O)NH | — $CH_2(CH)_2$ | H, H | $3,4\text{-}(MeO)_2PhSO_2NH$, H | H | H; |
| 3,4-dihydro-2H-pyrrol-5-yl | NH | — $CH_2(CH)_2$ | H, H | $3,4\text{-}(MeO)_2PhSO_2NH$, H | H | H; |
| benzyl | NHC(O)NH | — $CH_2(CH)_2$ | H, H | $4\text{-MeO-2,6-}Me_3PhSO_2NH$, H | H | H; |
| benzyl | NHC(O)NH | — $CH_2(CH)_2$ | H, H | $4\text{-MeOPhSO}_2NH$, H | H | H; |
| i-propyl | NHC(O)NH | — $CH_2(CH_2)$ | H, H | $(Me_5)PhSO_2NH$, H | H | H; |
| methyl | NHC(O)NH | — $CH_2(CH)_2$ | H, H | $(Me_5)PhSO_2NH$, H | H | H; |
| 3,4,5,6-tetrahydro-2-pyridinyl | NH | — $CH_2(CH)_2$ | H, H | $3,4\text{-}(MeO)_2PhSO_2NH$, H | H | H; |
| 3,4-dihydro-4-oxo-2-quinazolinyl | NH | — $CH_2(CH)_2$ | H, H | $(Me_5)PhSO_2NH$, H | H | H; |
| benzyl | NH C(O)NH | — $CH_2(CH)_2$ | H, H | $2,4,6\text{-}Me_3PhSO_2NH$, H | H | H; |
| 4,5-dihydro-1H-imidazol-2-yl | NH | — $CH_2(CH)_2$ | H, H | $4\text{-MeOPhOC(O)NH}$, H | H | H; |
| i-propyl | NH C(O)NH | — $CH_2C(CH)_2$ | H, H | $(Me_5)PhSO_2NH$, H | H | H; |
| benzyl | NH C(O)NH | — $CH_2(CH)_2$ | H, H | $5\text{-Cl-1,3-}Me_2\text{-1H-pyrazol-4-yl}SO_2NH$, H | H | H; |
| 2-Ph cyclopropyl | NH C(O)NH | — $CH_2(CH)_2$ | H, H | $(Me_5)PhSO_2NH$, H | H | H; |
| 3,4-dihydro-2H-pyrrol-5-yl | NH | — $CH_2(CH)_2$ | H, H | $PhCH_2OC(O)NH$, H | H | H; |
| 3,4,5,6,7,8-hexahydro-2-azocinyl | NH | — $CH_2(CH)_2$ | H, H | $3,4\text{-}(MeO)_2Ph\ SO_2NH$, H | H | H; |
| 4-Me-2-pyridinyl | NH | — $CH_2(CH)_2$ | H, H | $PhCH_2OC(O)NH$, H | H | H; |
| benzyl | NHC(O)NH | — $CH_2(CH)_2$ | H, H | $PhCH_2SO_2NH$, H | H | H; |
| 3,4,5,6-tetrahydro-2H-azepin-7-yl | NH | — $CH_2(CH)_2$ | H, H | $(CH_3)_3COC(O)NH$, H | H | H; |
| benzyl | NHC(O)NH | — $CH_2(CH)_2$ | H, H | 2-thienyl$SO_2NH$, H | H | H; |
| benzyl | NHC(O)NH | — $CH_2(CH)_2$ | H, H | n-butyl$SO_2NH$, H | H | H; |
| 3,4,5,6-tetrahydro-2H-azepin-7-yl | NH | — $CH_2(CH)_2$ | H, H | $(Me_5)PhSO_2NH$, H | H | H; |
| cyclohexyl | NHC(O)NH | — $CH_2(CH)_2$ | H, H | $(Me_5)PhSO_2NH$, H | H | H; |
| benzyl | NHC(O)NH | — $CH_2(CH)_2$ | H, H | 1-naphthalenyl-$(CH_2)_2SO_2NH$, H | H | H; |
| benzyl | NHC(O)NH | — $CH_2(CH)_2$ | H, H | $4\text{-MeOPhOC(O)NH}$, H | H | H; |
| 4,5-dihydro-1H-imidazol-2-yl | NH | — $CH_2(CH)_2$ | Ph, H | H, H | $CH_3$ | H; |

-continued

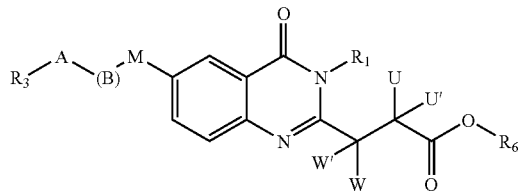

Formula (Ia)

wherein $R_3$, A, (B), M, W, W', U, U', $R_1$ and $R_6$ are dependently selected from the group consisting of

| $R_3$ | A | (B) M | W, W' | U, U' | $R_1$ | $R_6$ |
|---|---|---|---|---|---|---|
| cyclohexyl | NHC(O)NH | — CHC(CH$_3$) | H, H | (Me$_5$)PhSO$_2$NH, H | H | H; |
| phenethyl | NHC(O)NH | — CH$_2$(CH)$_2$ | H, H | (Me$_5$)PhSO$_2$NH, H | H | H; |
| 4-Me-2-oxazolyl and | NH | — CH$_2$(CH)$_2$ | H, H | (Me$_5$)PhSO$_2$NH, H | H | H; |
| 2-pyridinyl | NH | — CH$_2$(CH)$_2$ | H, H | H, H | PhCH$_2$ | H; | or a pharmaceutically acceptable racemate, enantiomer, diastereomer, or salt thereof.

44. A pharmaceutical composition comprising a compound of claim 1 and a pharmaceutically acceptable carrier.

45. A process for making a pharmaceutical composition comprising mixing a compound of claim 1 and a pharmaceutically acceptable carrier.

* * * * *